(12) United States Patent
Hagiwara et al.

(10) Patent No.: US 10,016,165 B2
(45) Date of Patent: Jul. 10, 2018

(54) INFORMATION PROCESSING APPARATUS, INFORMATION PROCESSING METHOD, AND PROGRAM

(75) Inventors: Takehiro Hagiwara, Tokyo (JP); Naoki Kamimaeda, Kanagawa (JP); Masanori Miyahara, Tokyo (JP); Yasutaka Fukumoto, Tokyo (JP); Masatomo Kurata, Tokyo (JP)

(73) Assignee: Sony Corporation (JP)

( * ) Notice: Subject to any disclaimer, the term of this patent is extended or adjusted under 35 U.S.C. 154(b) by 385 days.

(21) Appl. No.: 13/488,694

(22) Filed: Jun. 5, 2012

(65) Prior Publication Data
US 2012/0317064 A1 Dec. 13, 2012

(30) Foreign Application Priority Data

Jun. 13, 2011 (JP) ................ 2011-131073

(51) Int. Cl.
| | |
|---|---|
| G06F 17/00 | (2006.01) |
| A61B 5/00 | (2006.01) |
| A61B 5/11 | (2006.01) |
| A61B 5/16 | (2006.01) |
| G06Q 30/02 | (2012.01) |
| G06F 19/00 | (2018.01) |
| A61B 5/22 | (2006.01) |

(52) U.S. Cl.
CPC .......... *A61B 5/6898* (2013.01); *A61B 5/1118* (2013.01); *A61B 5/165* (2013.01); *G06F 19/3481* (2013.01); *G06Q 30/0201* (2013.01); *A61B 5/1112* (2013.01); *A61B 5/1123* (2013.01); *A61B 5/222* (2013.01); *A61B 2562/0219* (2013.01)

(58) Field of Classification Search
USPC ................................ 706/15, 45
See application file for complete search history.

(56) References Cited

U.S. PATENT DOCUMENTS

| | | | |
|---|---|---|---|
| 2008/0109257 A1* | 5/2008 | Albrecht ............... | G06F 19/345 705/2 |
| 2010/0191697 A1 | 7/2010 | Fukumoto et al. | |

(Continued)

FOREIGN PATENT DOCUMENTS

| | | |
|---|---|---|
| JP | 2010-198595 A | 9/2010 |
| JP | 2011-081431 A | 4/2011 |

(Continued)

OTHER PUBLICATIONS (With C.-Y. Lin, L.-J. Chen, and Y.-Y. Chen), "A Comfort Measuring System for Public Transportation Systems Using Participatory Phone Sensing", International Workshop on Sensing for App Phones (PhoneSense), Zurich, Switzerland, Nov. 2, 2010, pp. 1-5.*

(Continued)

*Primary Examiner* — David R Vincent
(74) *Attorney, Agent, or Firm* — Lerner, David, Littenberg, Krumholz & Mentlik, LLP

(57) ABSTRACT

An information processing apparatus may include a processor to acquire information associated with behavior of a user and information associated with satisfaction degree of the user, and to analyze an association between the information associated with behavior and the information associated with satisfaction degree.

19 Claims, 21 Drawing Sheets

(56) References Cited

U.S. PATENT DOCUMENTS

| | | | | |
|---|---|---|---|---|
| 2010/0218118 | A1* | 8/2010 | Bronkema | 715/751 |
| 2011/0081634 | A1 | 4/2011 | Kurata et al. | |
| 2011/0161107 | A1* | 6/2011 | Goldberg | G06F 19/3418 705/3 |

FOREIGN PATENT DOCUMENTS

| | | | |
|---|---|---|---|
| JP | 2011070501 A | 4/2011 | |
| JP | 2012503822 A | 2/2012 | |
| WO | 03046764 A1 | 6/2003 | |
| WO | 2010036477 A2 | 4/2010 | |
| WO | 2010146811 A1 | 12/2010 | |

OTHER PUBLICATIONS

Tsai, Lee, Raab, Norman, Sohn, Griswold, Patrick, "Usability and feasibility of PmEB: a mobile phone application for monitoring real time caloric balance", Journal Mobile Networks and Applications archive vol. 12 Issue 2-3, Mar. 2007 pp. 173-184.*

Leal-Taixe, Pons-Moll, Rosenhahn, "Exploiting Pedestrian Interaction via Global Optimization and Social Behaviors", Proceeding Proceedings of the 15th international conference on Theoretical Foundations of Computer Vision: outdoor and large-scale real-world scene analysis, Jun. 25, 1911, pp. 1-26.*

Daniel Kahneman, Alan B. Krueger, David A. Schkade, Norbert Schwarz, Arthur A. Stone, "A Survey Method for Characterizing Daily Life Experience: The Day Reconstruction Method", Science, vol. 306, Dec. 3, 2004, pp. 1776-1780.*

Louis Leung, Paul S.N. Lee, "Multiple determinants of life quality: the roles of Internet activities, use of new media, social support, and leisure activities", Telematics and Informatics, vol. 22, Apr. 13, 2004, pp. 161-180.*

Predrag Klasnja, Sunny Consolvo, David W. McDonald, James A. Landay, Wanda Pratt, "Using Mobile & Personal Sensing Technologies to Support Health Behavior Change in Everyday Life: Lessons Learned", American Medical Informatics Association Annual Symposium 2009 (AMIA 2009) Symposium Proceedings, 2009, pp. 338-342.*

Kiran K. Rachuri, Mirco Musolesi, Cecilia Mascolo, Peter J. Rentfrow, Chris Longworth, Andrius Aucinas, "EmotionSense: A Mobile Phones based Adaptive Platform for Experimental Social Psychology Research", The 2010 ACM Conference on Ubiquitous Computing Copenhagen, Denmark (UbiComp '10), Sep 26-29, 2010, pp. 281-290.*

Jingtao, Wang, "Perceptual and Context Aware Interfaces on Mobile Devices", Phd Thesis published by Computer Science, UC Berkeley, California, 2010, pp. 1-119.*

Nicholas D. Lane, Mashfiqui Mohammod, Mu Lin, Xiaochao Yang, Hong Lu, Shahid Ali, Afsaneh Doryab, Ethan Berke, Tanzeem Choudhury, Andrew T. Campbell, "BeWell: A Smartphone Application to Monitor, Model and Promote Wellbeing", 5th international ICST conference on pervasive computing technologies for healthcare, May 23, 2011, pp. 23-26.*

Japanese Office Action for JP Application No. 2011131073, dated Dec. 2, 2014.

Chinese Office Action for Application No. 201210185670.6 dated May 30, 2016.

* cited by examiner

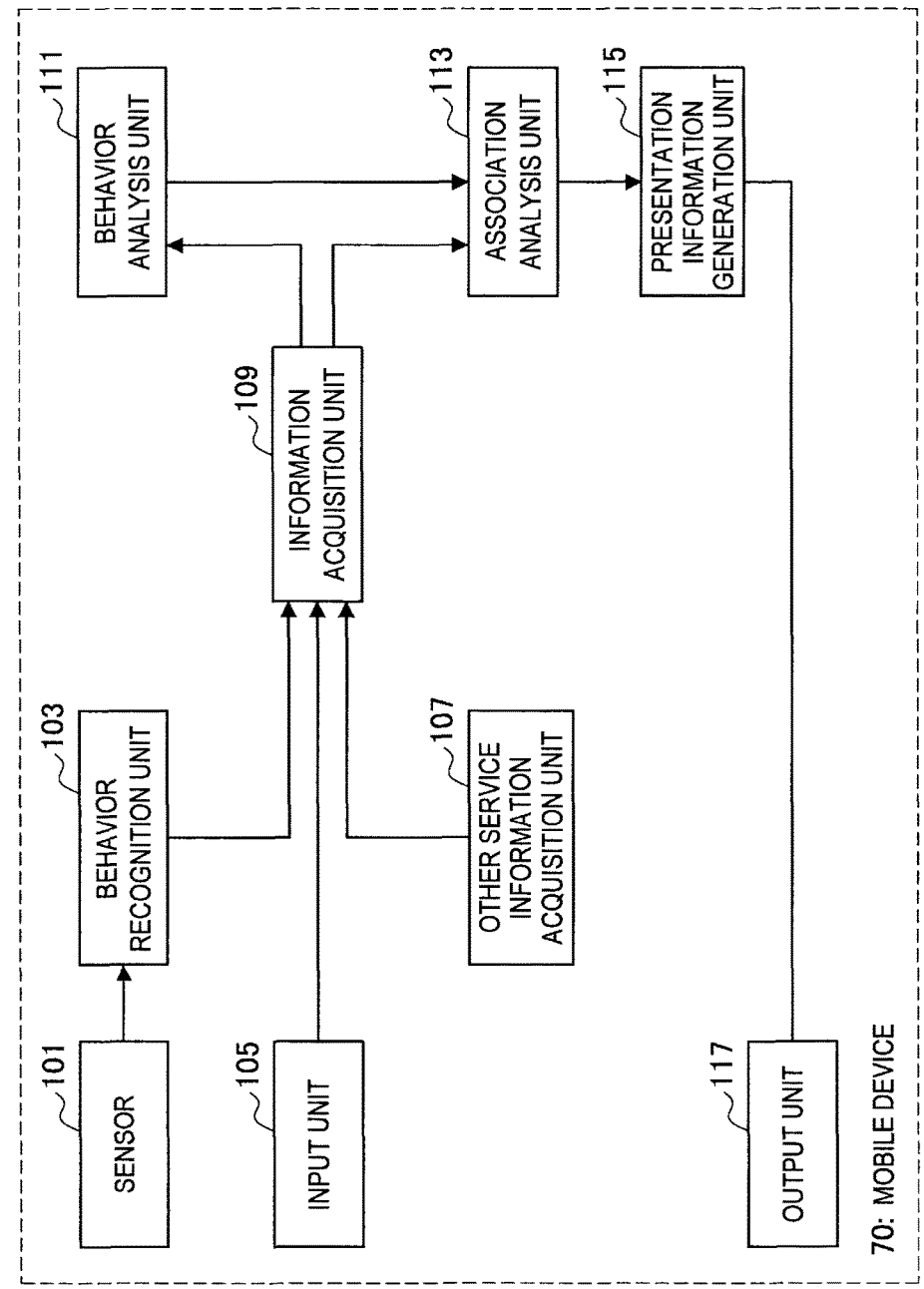

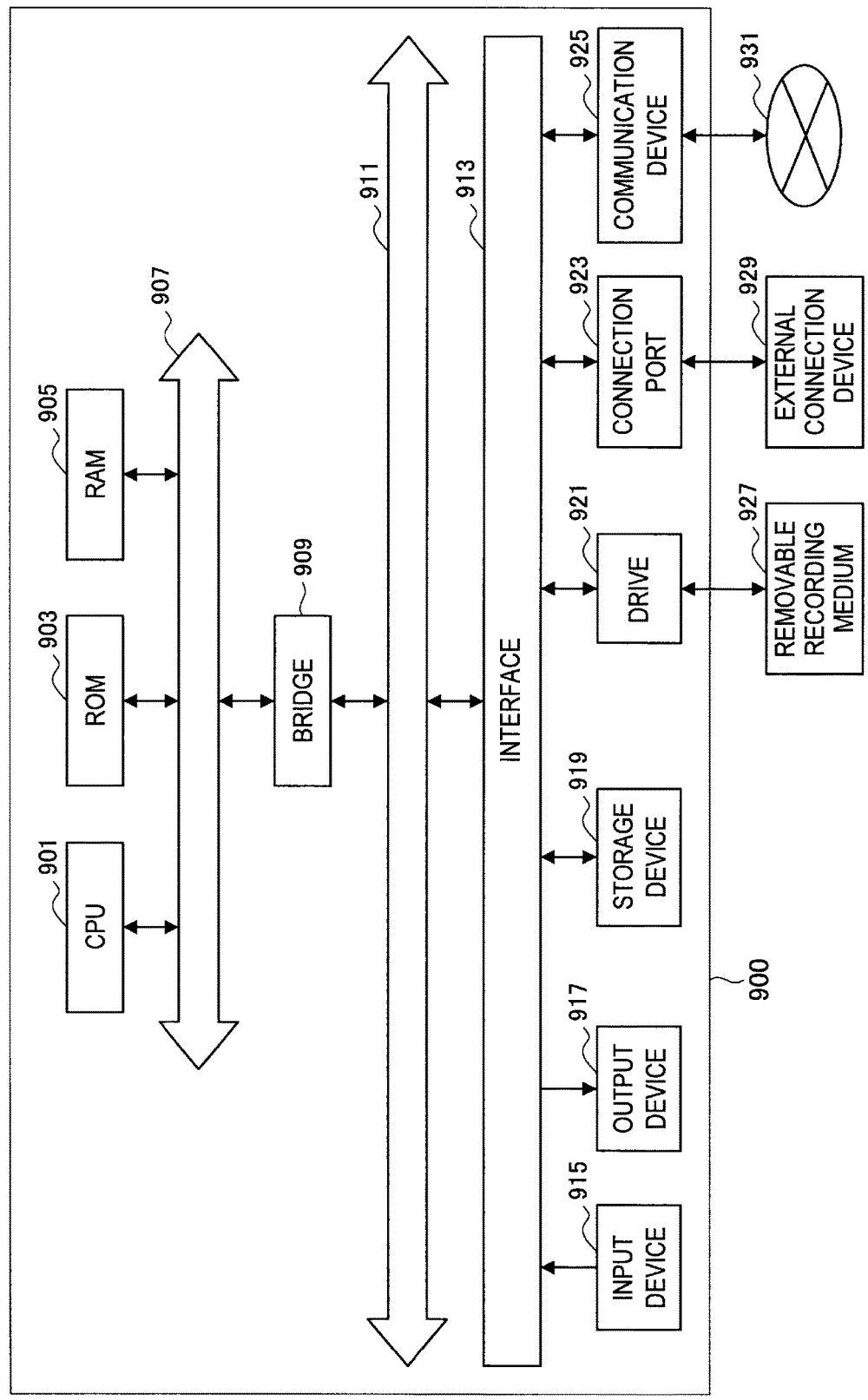

INFORMATION PROCESSING APPARATUS, INFORMATION PROCESSING METHOD, AND PROGRAM

CROSS-REFERENCE TO RELATED APPLICATIONS

This application claims priority from Japanese Patent Application No. JP 2011-131073 filed in the Japan Patent Office on Jun. 13, 2011, the entire contents of which is hereby incorporated by reference.

BACKGROUND

The present disclosure relates to an information processing apparatus, an information processing method, and a program.

An algorithm for acquiring information regarding a user's acceleration and position, and the like using a motion sensor and the like mounted in a mobile terminal owned by the user and recognizing a user's behavior from the information has been developed. For example, technology for recognizing a user's behavior by a filtering or arithmetic device with higher accuracy is disclosed in Japanese Patent Application Laid-Open No. 2010-198595. In addition, technology for detecting a user's behavior pattern over a comparatively long time is disclosed in Japanese Patent Application Laid-Open No. 2011-81431. Information on the behavior detected using the technology as described above is used, for example, to evaluate the behavior according to an index value such as an amount of exercise or calorie consumption or provide service corresponding to a situation of the user according to an application of a mobile terminal.

SUMMARY

However, a personal situation or property of a user who receives the provision of services is not necessarily considered because the use of the behavior information as described above is based on, for example, a reference value of an amount of exercise or calorie consumption statistically calculated, a thought pattern of a general user, and the like. Therefore, there is room for further improvement in that a satisfaction degree of the user is increased by the provision of services using the recognized behavior information of the user.

The present disclosure provides a novel and improved information processing apparatus, information processing system, and program that can help a user perform behavior by which a higher satisfaction degree can be obtained.

In accordance with one embodiment, an information processing apparatus may include a processor to acquire information associated with behavior of a user and information associated with satisfaction degree of the user, and to analyze an association between the information associated with behavior and the information associated with satisfaction degree.

In accordance with another embodiment, an information processing apparatus may include a processor to generate information that affects behavior of a user in accordance with an analyzed association between information associated with behavior of the user and information associated with satisfaction degree of the user, where the information associated with behavior and the information associated with satisfaction degree are acquired.

In accordance with another embodiment, a method of information processing may include acquiring information associated with behavior of a user and information associated with satisfaction degree of the user. In addition, the method may include analyzing, by a processor, an association between the information associated with behavior and the information associated with satisfaction degree.

In accordance with another embodiment, a non-transitory recording medium may be recorded with a program executable by a computer, where the program includes acquiring information associated with behavior of a user and information associated with satisfaction degree of the user, and analyzing an association between the information associated with behavior and the information associated with satisfaction degree.

BRIEF DESCRIPTION OF THE DRAWINGS

FIG. 20 is a block diagram showing a functional configuration of an information processing system according to a second embodiment of the disclosure; and FIG. 21 is a block diagram illustrating a hardware configuration of an information processing apparatus.

DETAILED DESCRIPTION OF THE EMBODIMENT(S)

Figure 1:
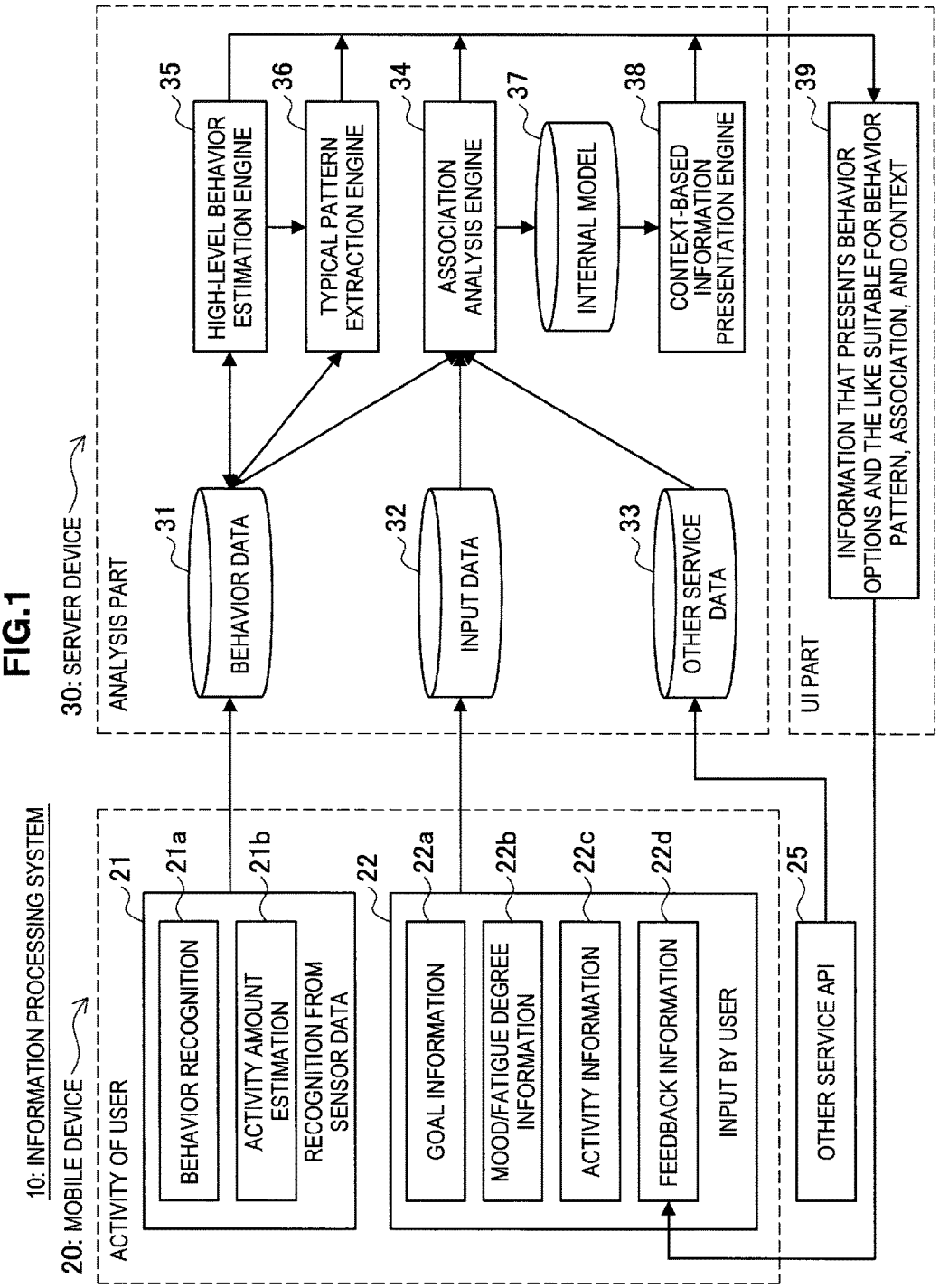
FIG. 1 is a diagram schematically illustrating a configuration of an information processing system according to a first embodiment of the disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

Description will be given in the following order.
1. First Embodiment
1-1. Configuration of Information Processing System
1-2. Flow of Process
1-3. Example of Information Input
1-4. Example of Information Presentation
2. Second Embodiment
3. Hardware Configuration
4. Supplement

First Embodiment

Hereinafter, the first embodiment of the disclosure will be described. First, a configuration of an information processing system according to this embodiment will be described with reference to FIGS. 1 to 3. Next, a flow of a process according to this embodiment will be described with reference to FIGS. 4 and 5. Further, an example of an information input according to this embodiment will be described with reference to FIGS. 6 to 11. Finally, an example of information presentation according to this embodiment will be described with reference to FIGS. 12 to 19.

(1-1. Configuration of Information Processing System)

Figure 2:
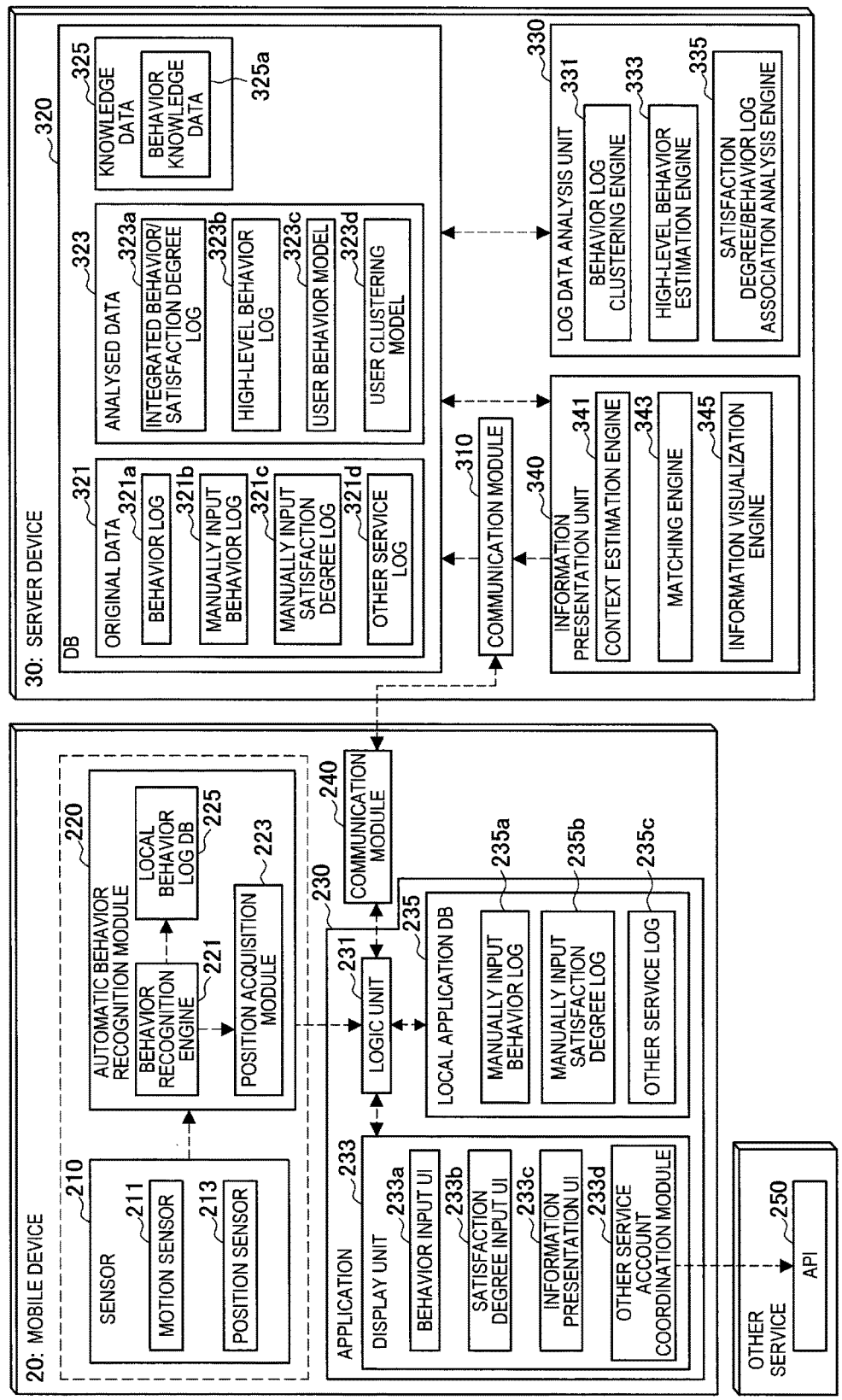
FIG. 2 is a diagram illustrating further details of the configuration of the information processing system according to the first embodiment of the disclosure.
Figure 3:
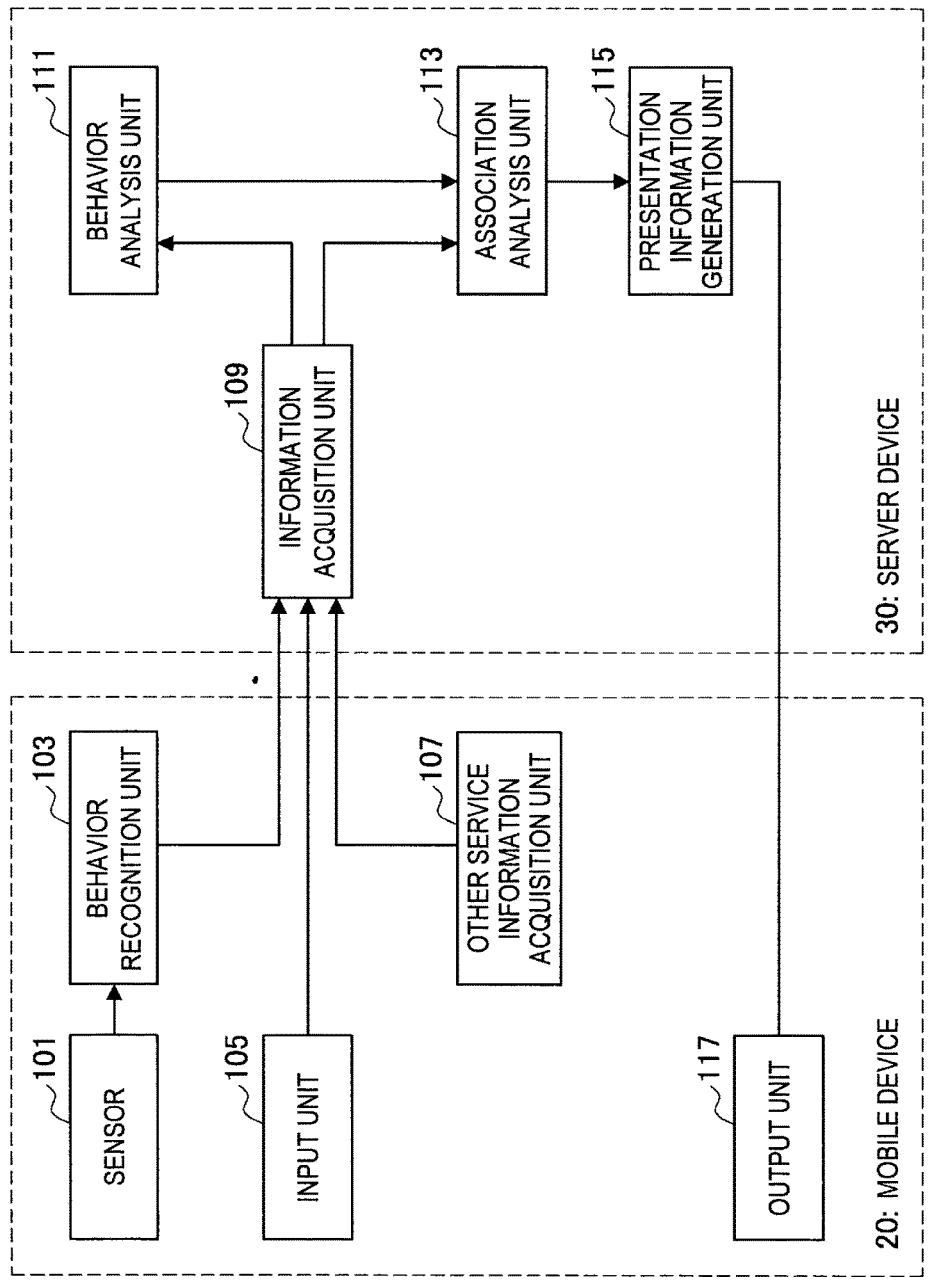
FIG. 3 is a block diagram showing a functional configuration of the information processing system according to the first embodiment of the disclosure.

First, the configuration of the information processing system according to this embodiment will be described. In the following description, the configuration of the information processing system will be described with reference to the three drawings. FIG. 1 is a diagram schematically illustrating the configuration of the information processing system, FIG. 2 is a diagram illustrating further details of the configuration shown in FIG. 1, and FIG. 3 is a diagram in which the configuration shown in FIGS. 1 and 2 is expressed by a functional block diagram.

(1-1-1. Schematic Description)

FIG. 1 is a diagram schematically illustrating the configuration of the information processing system according to the first embodiment of the disclosure. In this embodiment, the information processing system 10 includes a mobile device 20 and a server device 30.

The mobile device 20 is a portable device of the user. The mobile device 20 serves as a client in a relationship with the server device 30. The mobile device 20 acquires information on activities of a user and transmits the information to the server device 30. In addition, the mobile device 20 presents information received from the server device 30 to the user.

As long as such functions can be implemented, the mobile device 20 is not limited to a general mobile device. That is, the mobile device 20 may be various devices such as a tablet or notebook personal computer (PC), a game machine, and a personal digital assistant (PDA) as well as a smart phone or a mobile phone.

In addition, the functions of the mobile device 20 may not be necessarily implemented by a single device. For example, a function of acquiring information 21 recognized from sensor data is implemented by a smart phone carried by the user and a function of acquiring information 22 input by the user and a function of presenting information to the user are implemented by a desktop PC of the user, so that the functions may each be implemented by separate devices.

On the other hand, the server device 30 has an analysis part for storing and analyzing information received from the mobile device 20, which is the client, and a UI part for generating information on the basis of a result of analysis. Here, the generated information is transmitted to the mobile device 20 and presented to the user. Although the mobile device 20 and the server device 30 have a 1:1 relationship in the illustrated example, the server device 30 may communicate with a plurality of mobile devices 20 used by a plurality of users.

As long as such functions can be implemented, the server device 30 may be any type of device. For example, the server device 30 may be a single device or a cluster of resources distributed to a plurality of devices in a network.

Information acquired in the mobile device 20 includes the information 21 recognized from the sensor data and the information 22 input by the user. Here, the information 21 recognized from the sensor data includes behavior recognition information 21a and activity amount estimation information 21b. It is possible to recognize or estimate the user's behavior or the activity amount from information on the user's acceleration or position detected as the sensor data by an engine using a well-known algorithm, for example, as in the technology disclosed in Japanese Patent Application Laid-Open No. 2010-198595.

On the other hand, the information 22 input by the user includes goal information 22a, mood/fatigue degree information 22b, activity information 22c, and feedback information 22d. The goal information 22a is a goal the user wants to accomplish through activity, for example, an amount of exercise, calorie consumption, or the like. The mood/fatigue degree information 22b is an index of a subjective satisfaction degree of the user. The activity information 22c is information of a label the user himself/herself assigns to behavior, such as information indicating what the user is doing now (at an input time), who the user is with, or how the user feels. The feedback information 22d is information on feedback of the user for the behavior presented by the information processing system 10 as will be described later.

The information input in the mobile device 20 is transmitted to the server device 30 at any time or periodically. The server device 30 stores the information 21 recognized from the sensor data in the mobile device 20 as behavior data 31. In addition, the information 22 input by the user in the mobile device 20 is stored as input data 32.

Further, in the server device 30, data acquired from an other service application programming interface (API) 25 is stored as other service data 33. The other service data 33 may be, for example, content of a log the user has spoken in communication on a network, or the like.]

Next, data stored as the behavior data 31, the input data 32, and the other service data 33 is analyzed in the server device 30. Here, the analyzed data is not limited to data regarding a single user, and may be data regarding a plurality of users. That is, the server device 30 may communicate with a plurality of mobile devices 20 and store and analyze the data regarding the plurality of users.

Engines such as an association analysis engine 34, a high-level activity estimation engine 35, and a typical pattern extraction engine 36 may be used for the analysis of data in the server device 30. The association analysis engine 34 analyzes a relationship between the user's behavior and the user's satisfaction degree in a period including the behavior by integrally analyzing the behavior data 31, the input data 32, and the other service data 33. The high-level activity estimation engine 35 estimates "work" or "shopping" and higher-order behavior of the user such as "work" using the well-known algorithm, for example, as in the technology disclosed in Japanese Patent Application Laid-Open No. 2011-81431. The typical pattern extraction engine 36 extracts a typical pattern of behavior of the user.

Further, the user device 30 may generate and update an internal model 37 on the basis of an analysis result of the association analysis engine 34, and generate information regarding context-based behavior presented to the user using the context-based information presentation engine 38 on the basis of the internal model 37.

The server device 30 generates information 39 for presenting behavior options suitable for a behavior pattern, an association, and a context on the basis of the above-described analysis result as information presented to the user. The information 39 is transmitted to the mobile device 20 and presented to the user.

Here, a mobile device 20 (a second mobile device) to which the information 39 is transmitted may not necessarily be the same device as a mobile device 20 (a first mobile device) transmitting the information regarding the user's behavior to the server device 30. For example, the second mobile device may be the mobile device 20 used by a family of the user using the first mobile device, and the information 39 may be indirectly provided to the user in the form of advice from the family to the user.

(1-1-2. Further Detailed Description)

FIG. 2 is a diagram illustrating further details of the configuration of the information processing system according to the first embodiment of the disclosure. As described above, in this embodiment, the information processing system 10 includes the mobile device 20 and the server device 30. The mobile device 20 includes a sensor 210, an automatic behavior recognition module 220, an application 230, and a communication module 240. The server device 30 includes a communication module 310, a database (DB) 320, a log data analysis unit 330, and an information presentation unit 340.

(Sensor)

The sensor 210 includes a motion sensor 211 and a position sensor 213. Here, the motion sensor 211 includes, for example, a triaxial acceleration sensor (including an acceleration sensor, a gravity detection sensor, a drop detection sensor, and the like) or a triaxial gyro sensor (including an angular velocity sensor, a camera-shake correction sensor, a geomagnetism sensor, and the like), and detects an acceleration change and a rotation around the gravity axis when the user has performed behavior. The position sensor 213 detects a position of the user using a global positioning system (GPS), a wireless local area network (LAN), or a mobile network. Further, the sensor 210 may detect information indicating "whether or not a device has been used," "which application has been used," or the like by acquiring an operation log of the mobile device 20, or detect a temperature, humidity, ambient sound, brightness, and the like. The sensor 210 provides the detected information to the automatic behavior recognition module 220.

(Automatic Behavior Recognition Module)

The automatic behavior recognition module 220 includes a behavior recognition engine 221, a position acquisition module 223, and a local behavior log DB 225. The automatic behavior recognition module 220 may be implemented, for example, by a central processing unit (CPU), a random access memory (RAM), a read only memory (ROM), and the like in the mobile device 20.

Here, the behavior recognition engine 221 is an engine that recognizes the user's behavior or an activity amount using an algorithm, for example, as in the technology disclosed in Japanese Patent Application Laid-Open No. 2010-198595. The behavior recognition engine 221 recognizes a type of behavior such as "walk/run," "jump," "stand/sit," or "bicycle/car/elevator/train/bus," or the strength of an activity such as "activity amount," "number of steps," or "pitch."

The position acquisition module 223 acquires a position of the user from a result of detection of the position sensor 213. The position acquisition module 223 may remove noise from the detection result of the position sensor 213 so as to improve the accuracy of the position. The position acquisition module 223 acquires information, for example, such as "latitude/longitude," "moving velocity," "altitude," and "outdoor/indoor," as information regarding the position of the user.

The local behavior log DB 225 temporarily stores information regarding the user's behavior acquired by the behavior recognition engine 221 and the position acquisition module 223 as a log.

The automatic behavior recognition module 220 provides information regarding the recognized behavior of the user to the logic unit 231 of the application 230. This information serves as the information 21 described with reference to FIG. 1. The sensor 210 and the automatic behavior recognition module 220 may be separated as different devices from the application 230 and the communication module 240. In this case, the above-described information may be provided from the automatic behavior recognition module 220 to the logic unit 231 via communication using a communication module of each device.

(Application)

The application 230 is, for example, an application provided by a program executable by the CPU, the RAM, the ROM, and the like in the mobile device 20. The application 230 includes a logic unit 231, a display unit 233, and a local application DB 235.

Here, the logic unit 231 provides a logic that controls an input/output of information of the application 230. For example, the logic unit 231 transmits information provided from the automatic behavior recognition module 220 to the communication module 240 for transmission to the server device 30. In addition, the logic unit 231 temporarily stores information input by a UI provided by the display unit 233 in the local application DB 235 or provides the stored information to the communication module 240 by reading the information from the local application DB 235. Further, the logic unit 231 provides the display unit 233 with presentation information for the user received by the communication module 240 from the server device 30.

The display unit 233 executes the information acquisition and the information presentation by the application 230. The display unit 233 controls an image to be displayed on a display of the mobile device 20 or acquires information input by the user via an input device such as a touch panel or keyboard of the mobile device 20. Here, the acquired information serves as the information 22 described with reference to FIG. 1. The display unit 233 includes a behavior input UI 233*a*, a satisfaction degree input UI 233*b*, an information presentation UI 233*c*, and an other service account coordination module 233*d*.

The behavior input UI 233*a* is a UI for allowing the user to input information regarding behavior. The behavior input UI 233*a* acquires, for example, information of a behavior label indicating what the user is doing at the time or what the user did at a certain past time (for example, afternoon of the same day when information is input at night). The information of the behavior label is information that specifies the behavior of the user at the time, for example, such as "work," "eat," "wake-up," "sleep," "study," "housework," or the like. The information on the behavior label may be input by selection from a predetermined item and input by selection from an item arbitrarily added by the user. In addition, the behavior input UI 233*a* may acquire information indicating who the user is with at the time or who the user was with at a certain past time. Further, the behavior input UI 233*a* may acquire information on a goal the user achieves through behavior. The behavior input UI 233*a* may associate the information with information of an input time or a time specified by an input to provide the associated information to the logic unit 231. A specific example of the behavior input UI will be described later as an example of an information input.

The satisfaction degree input UI 233*b* is a UI for allowing the user to input information on a satisfaction degree in a period including behavior recognized by the automatic behavior recognition module 220. The satisfaction degree input UI 233*b* acquires a satisfaction degree felt at behavior when the user inputs information or behavior at a certain past time in the form of step-by-step evaluation or the like. Here, the information on the satisfaction degree input by the user does not necessarily indicate the satisfaction degree at the input time. For example, the information may indicate a satisfaction degree in any period before the input so that the satisfaction degree felt in the morning is largely affected by the behavior of a previous day. A definition or measure for expressing the satisfaction degree may be variously set. The satisfaction degree may be expressed by criteria, for example, such as "stress," "refreshment degree," "sleepy," "fatigue," "concentration power," and "mood." The user may select one of the criteria or use a combination of a plurality of criteria. In addition, the user may input the satisfaction degree by the criteria, and input the satisfaction degree as a total score of a plurality of criteria. In addition, the satisfaction degree input UI 233*b* may acquire comments or memos input by the user. For example, it is also possible to extract information regarding the behavior or satisfaction degree of the user by filtering from character information such as the comments or memos. The satisfaction degree input UI 233*b* may associate the information with information of an input time or a time specified by an input and provide the associated information to the logic unit 231. A specific example of the satisfaction degree input UI 233*b* will be described as an example of an information input.

The information presentation UI 233*c* is a UI for presenting information regarding behavior to the user. As described above, the information acquired in the mobile device 20 is analyzed by the server device 30, and information to be presented to the user is generated on the basis of a result of analysis. The information presentation UI 233*c* is a UI for acquiring the information from the logic unit 231 and presenting the acquired information to the user. The information presentation UI 233*c* may present, for example, desirable behavior information for the user to the user, for example, as "Present recommended activity," "Your best behavior," or the like. In addition, the information presentation UI 233*c* may present information regarding a behavior pattern of the user to the user, for example, as "Today's activity," "Your ideal behavior plan," or the like. Further, the information presentation UI 233*c* may present information regarding behavior patterns of other users related to the behavior pattern of the user to the user, for example, as "Recent activity of someone like you" or the like. In addition, the information presentation UI 233*c* may include a UI for receiving feedback from the user with respect to the presented information, and provide the acquired feedback information to the logic unit 231. A specific example of the information presentation UI 233*c* will be described as an example of information presentation.

The other service account coordination module 233*d* acquires information input by the user in another service, for example, by accessing the other service API 250 using account information of the user in the other service. The other service used here may be, for example, a communication service to which the user inputs text data as "speech" or a social service. The other service account coordination module 233*d* acquires, for example, information regarding when the user's speech has been made and content of "speech" in the other service, and provides the information to the logic unit 231.

The local application DB 235 is implemented, for example, by a storage device of the mobile device 20. The local application DB 235 temporarily stores information acquired from the input of the user in the application 230. The local application DB 235 includes a manually input behavior log 235*a*, a manually input satisfaction degree log 235*b*, and an other service log 235*c*. These DBs each store information acquired by the behavior input UI 233*a*, the satisfaction degree input UI 233*b*, and the other service account coordination module 233*d* of the display unit 233.

(Communication Module)

The communication modules 240 and 310 are modules for communication between the mobile device 20 and the server device 30. The communication modules 240 and 310 may be implemented, for example, by various communication devices corresponding to types of communication networks between the mobile device 20 and the server device 30.

(DB of Server Device)

The DB 320 is implemented, for example, by a storage device of the server device 30. The DB 320 stores data acquired from the mobile device 20, data as results of data analysis, and other data to be used for the analysis. The DB 320 includes original data 321, post-analysis data 323, and knowledge data 325. As correspondence between the information stored in the DB 320 and the data described with reference to FIG. 1, a behavior log 321*a* may correspond to the behavior data 31, a manually input behavior log 321*b* and a manually input satisfaction degree log 321*c* may correspond to the input data 32, an other service log 321d may correspond to the other service data 33, and the user behavior model 323c and the user clustering model 323d may correspond to the internal model 37.

The original data 321 includes the behavior log 321a, the manually input behavior log 321b, the manually input satisfaction degree log 321c, and the other service log 321d. Among these, information regarding the user's behavior acquired by the automatic behavior recognition module 220 of the mobile device 20, that is, information on the user's behavior automatically recognized by a behavior recognition algorithm, is stored in the behavior log 321a. Information regarding the user's behavior acquired by the behavior input UI 233a of the mobile device 20, that is, a behavior label independently input by the user, information indicating who the user is with, or the like, is stored in the manually input behavior log 321b. Information regarding the user's satisfaction degree acquired by the satisfaction degree input UI 233b of the mobile device 20 is stored in the manually input satisfaction degree log 321c. Information such as a log of another service acquired by the other service account coordination module 233d of the mobile device 20 is stored in the other service log 321d.

The post-analysis data 323 is data as results after the log data analysis unit 330 has analyzed the original data 321, and includes an integrated behavior/satisfaction degree log 323a, a high-level behavior log 323b, the user behavior model 323c, and the user clustering model 323d. Among these, the integrated behavior/satisfaction degree log 323a is a log into which various logs included in the original data 321 have been integrated. The high-level behavior log 323b is a log of higher-order behavior of the user estimated on the basis of the original data 321. Here, the higher-order behavior is behavior performed over a comparatively long time, for example, for any purpose for "work," "shopping," or the like. The user behavior model 323c is a model into which the user's behavior is classified. For example, there may be a plurality of types of behavior models reflecting a typical pattern or habitual property for each user. An example of the user clustering model 323d is a model obtained by clustering users whose behaviors or satisfaction degrees are similar when the server device 30 collects information regarding behaviors or satisfaction degrees of a plurality of users.

The knowledge data 325 is data prepared for analysis in the log data analysis unit 330. The knowledge data 325 includes behavior knowledge data 325a.

For example, the behavior knowledge data 325a is data related to behavior or physical limitations of a general user, such as "It is not possible to wake up for one week" or "It is not possible to continuously walk 10,000 km," in other words, common-sense data of behavior. The behavior knowledge data 325a may be defined, for example, for each type of behavior and strength of activity.

Some or all of data stored in the DB 320 may be stored, for example, in a virtual storage on a network outside the server device 30. That is, the server device 30 may not necessarily have the storage device storing the data of the DB 320.

(Log Data Analysis Unit)

The log data analysis unit 330 is implemented, for example, by a CPU, a RAM, a ROM, and the like in the server device 30. The log data analysis unit 330 includes a behavior log clustering engine 331, a high-level behavior estimation engine 333, and a satisfaction degree/behavior log association analysis engine 335. The log data analysis unit 330 includes functions corresponding to the high-level behavior estimation engine 35, the typical pattern extraction engine 36, and the association analysis engine 34 described with reference to FIG. 1.

Here, the behavior clustering engine 331 clusters behavior logs of the users using the behavior log 321a, the manually input behavior log 321b, and the like stored in the DB 320. The behavior log clustering engine 331 may integrate information by discretizing the manually input behavior log 321b on a time axis and supplementing a part in which information is missing using the behavior log 321a. In addition, the behavior log clustering engine 331 may supplement information of a missing part of the manually input behavior log 321b using behavior or physical limitations of a general user stored as the knowledge data 325 or a habitual property of behavior of the user reflected in a previously integrated behavior/satisfaction degree log 323a.

The high-level behavior estimation engine 333 estimates high-level behavior of the user using the technology, for example, as disclosed in Japanese Patent Application Laid-Open No. 2011-81431. The satisfaction degree/behavior log association analysis engine 335 analyzes a relationship between the user's behavior and the user's subjective satisfaction degree, for example, using the integrated behavior/satisfaction degree log 323a stored in the DB 320.

The log data analysis unit 330 re-stores data obtained by analysis in the DB 320 as the post-analysis data 323. A process of the log data analysis unit 330 will be described in further detail in the description of a flow of the process to be described later.

(Information Presentation Unit)

The information presentation unit 340 is implemented, for example, by the CPU, the RAM, the ROM, and the like in the server device 30. The information presentation unit 340 includes a context estimation engine 341, a matching engine 343, and an information visualization engine 345. The information presentation unit 340 includes a function corresponding to the context-based information presentation engine 38 described with reference to FIG. 1.

Here, the context estimation engine 341 estimates a context of behavior of the user, for example, using the post-analysis data 323 stored in the DB 320. The matching engine 343 generates information for recommending behavior suitable for a current situation of the user, for example, by matching behavior recommended on the basis of an association between the behavior and the satisfaction degree of the user analyzed by the satisfaction degree/behavior log association analysis engine 335 and the current situation of the user indicated by information newly acquired from the mobile device 20. The information visualization engine 345 converts information generated in the information presentation unit 340 in the form of presentation that is easily understandable to the user. For example, the information visualization engine 345 converts the generated information in the form of a numeric value of a score, a graph, or the like.

(1-1-3. Functional Block)

FIG. 3 is a block diagram showing a functional configuration of the information processing system according to the first embodiment of the disclosure. This block diagram is a diagram in which the configurations shown in FIGS. 1 and 2 are expressed by functional blocks.

The information processing system 10 includes the mobile device 20 and the server device 30. The mobile device 20 includes the sensor 101, the behavior recognition unit 103, the input unit 105, the other service information acquisition unit 107, and the output unit 117. The server device 30 includes an information acquisition unit 109, a behavior analysis unit 111, an association analysis unit 113, and a presentation information generation unit 115.

The sensor 101 has a function corresponding to the above-described sensor 210. The sensor 101 detects information on the acceleration or position of the user, and provides the information to the behavior recognition unit 103. A function of the sensor 101 may be implemented by a sensor such as a motion sensor or a position sensor mounted in the mobile device 20.

The behavior recognition unit 103 has a function corresponding to the above-described automatic behavior recognition module 220. The behavior recognition unit 103 recognizes the user's behavior by the behavior recognition algorithm from the information acquired from the sensor 101. The behavior recognition unit 103 may be implemented by the CPU, the RAM, the ROM, and the like in the mobile device 20.

The input unit 105 has functions corresponding to the behavior input UI 233a and the satisfaction degree input UI 233b in the above-described display unit 233. The input unit 105 receives an input such as a label assigned by the user for a satisfaction degree or behavior of the user, and acquires the input as information. The input unit 105 may be implemented by an input device such as a touch panel or a keyboard in the mobile device 20. An example of a UI for information acquisition by the input unit 105 will be described later.

The other service information acquisition unit 107 has a function corresponding to the other service account coordination module 233d in the above-described display unit 233. The other service information acquisition unit 107 acquires other service information input by the user for another service. The other service information acquisition unit 107 may be implemented by the CPU, the RAM, the ROM, and the like in the mobile device 20.

The information acquisition unit 109 may be implemented by the CPU, the RAM, the ROM, and the like in the server device 30, and may have an interface function for receiving data from the mobile device 20, which is a client. That is, the information acquisition unit 109 acquires information from the behavior recognition unit 103, the input unit 105, and the other service information acquisition unit 107 via the above-described communication modules 240 and 310. Here, the acquired information includes first behavior information, which is information on behavior of the user recognized by the behavior recognition algorithm, second behavior information, which is information input by the user in relation to the behavior, satisfaction degree information, which is information on the satisfaction degree of the user in a period including the behavior, and other service information, which is information input by the user for another service. The information acquisition unit 109 may further acquire feedback information from the user to which information indicating recommended behavior to be described later has been presented, or goal information, which is the user's goal related to the behavior. The information acquisition unit 109 provides the above-described information to the behavior analysis unit 111 and the association analysis unit 113. In addition, the information acquisition unit 109 may store the information in the above-described DB 320.

The behavior analysis unit 111 has functions corresponding to the behavior log clustering engine 331 and the high-level behavior estimation engine 333 in the above-described log data analysis unit 330. The behavior analysis unit 111 integrates behavior information acquired by the information acquisition unit 109 from the behavior recognition unit 103 and the input unit 105, thereby generating the integrated behavior information. The behavior analysis unit 111 is implemented by the CPU, the RAM, the ROM, and the like in the server device 30. Details of a process of the behavior analysis unit 111 will be described later.

The association analysis unit 113 has a function corresponding to the satisfaction degree/behavior log association analysis engine 335 in the above-described log data analysis unit 330. The association analysis unit 113 analyzes an association between the behavior and the satisfaction degree of the user using the information acquired from the information acquisition unit 109 and the behavior analysis unit 111. The association analysis unit 113 is implemented by the CPU, the RAM, the ROM, and the like in the server device 30. Details of a process of the association analysis unit 113 will be described later.

The presentation information generation unit 115 has a function corresponding to the above-described information presentation unit 340. The presentation information generation unit 115 generates information that affects the user's behavior on the basis of the association between the behavior and the satisfaction degree of the user analyzed by the association analysis unit 113. Here, the information that affects the user's behavior is information that directly or indirectly affects selection of behavior of the user and helps the user perform behavior of which a higher satisfaction degree is obtainable, such as information for comparing relationships between behavior patterns and satisfaction degrees between the user and other users, as well as information for presenting desirable/undesirable behavior to the user. The presentation information generation unit 115 may be implemented by the CPU, the RAM, the ROM, and the like in the server device 30. An example of information to be generated by the presentation information generation unit 115 will be described later.

The output unit 117 has a function corresponding to the information presentation UI 233c in the above-described display unit 233. The output unit 117 presents information acquired by the presentation information generation unit 115 via the above-described communication modules 240 and 310. The output unit 117 may be implemented by an output device such as a display of the mobile device 20.

The configuration of the information processing system according to this embodiment has been described above. In the following description, the components of the information processing system 10 will be referred to using the functional blocks shown in FIG. 3.

(1-2. Flow of Process)

Next, the flow of the process according to this embodiment will be described. In the following description, the entire process flow will first be described with reference to FIG. 4, the process of the behavior analysis unit 111 will next be described with reference to FIG. 5, and the process of the association analysis unit 113 will finally be described.

(1-2-1. Entire Flow)

Figure 4:
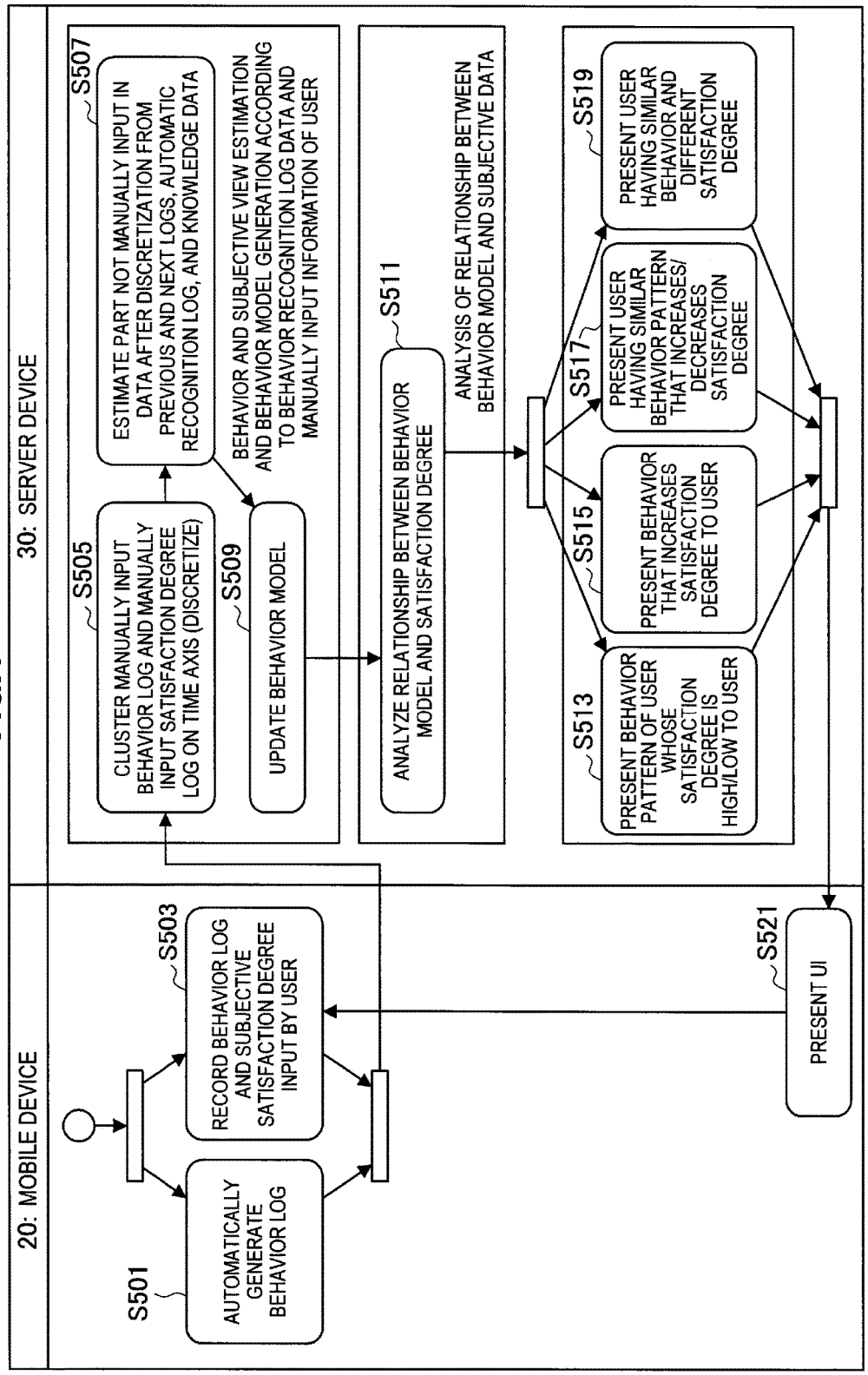
FIG. 4 is a diagram showing an example of a flow of a process according to the first embodiment of the disclosure.

FIG. 4 is a diagram showing an example of the flow of the process according to the first embodiment of the disclosure.

In the illustrated example, first, the behavior recognition unit 103 of the mobile device 20 automatically generates a behavior log by the behavior recognition engine using information acquired by the sensor 101 (step S501). On the other hand, the input unit 105 receives input records of a behavior log and a satisfaction degree log manually input by the user on the application 230 (step S503).

Next, information generated and recorded by the mobile device 20 is transmitted to the server device 30, and the information acquisition unit 109 acquires the information. In the server device 30, first, the behavior analysis unit 111 executes behavior and subjective-view estimation and behavior model generation by the behavior recognition data and the manually input information of the user (steps S505 to S509).

First, the behavior analysis unit 111 clusters the manually input behavior log 321b and the manually input satisfaction degree log 321c on the time axis (step S505). Next, the behavior analysis unit 111 estimates information of a missing part not input in the manually input behavior log 321b discretized by clustering using previously and next manually input behavior logs 321b, the automatically recognized behavior log 321a, and the knowledge data 325 (step S507). Here, the behavior analysis unit 111 estimates behavior of a missing part, for example, in a method of estimating probability distributions of previous and next behaviors from the manually input behavior log 321b, estimating high-level behavior using the behavior log 321a, generating a distribution function using the knowledge data 325, and employing behavior models of a target user and similar users. The behavior of the missing part may be estimated as a probability value. Details of the process of step S507 will be described later.

Next, the behavior analysis unit 111 updates a behavior model of the user using the integrated behavior log of step S507 (step S509). Here, the behavior model is a model into which the user's behavior is classified. For example, several types are prepared in consideration of a typical pattern or habitual property. The behavior model may be a vector model.

Next, the association analysis unit 113 analyzes a relationship between the behavior model of the user updated by the behavior analysis unit 111 and the satisfaction degree of the user acquired by the information acquisition unit 109 (step S511). Here, the association analysis unit 113 estimates or extracts a behavior pattern for maximizing or minimizing a subjective satisfaction degree, for example, using an algorithm such as Bayesian estimation, decision tree analysis, or discretization vector superposition.

Next, the presentation information generation unit 115 generates information to be presented to the user. Here, the presentation information generation unit 115 generates the information to be presented to the user by the process of one of steps S513 to S519.

In step S513, the presentation information generation unit 115 generates information for presenting a behavior pattern of which the user's satisfaction degree is high/low. In this case, the information presented to the user can make the user realize, for example, a relationship between his/her behavior and the satisfaction degree.

In step S515, the presentation information generation unit 115 generates information for presenting behavior that increases the future satisfaction degree of the user. In this case, the information presented to the user can support the user in performing behavior of which the satisfaction degree is higher.

In step S517, the presentation information generation unit 115 generates information for presenting other users similar to the user in terms of a behavior pattern that increases/decreases the satisfaction degree. In this case, the information presented to the user can make the user sympathize with other users having similarities, for example, by finding the other users similar to him/her.

In step S519, the presentation information generation unit 115 generates information for presenting other users similar to the user in terms of the behavior pattern, but different from the user in terms of a relationship between the behavior and the satisfaction degree. In this case, the information presented to the user can make the user refer to other users by finding the other users each having a different sense from him/her.

Next, the server device 30 transmits information generated in one of the steps S513 to S519 to the mobile device 20. In the mobile device 20, the output unit 117 presents the information to the user via the UI (step S521). In the mobile device 20, feedback information for the presented information may be further input by the user (step S503).

The flow of the entire process according to this embodiment has been described above. Hereinafter, processes of the behavior analysis unit 111 and the association analysis unit 113 will be described in further detail.

(1-2-2. Process of Behavior Analysis Unit)

Figure 5:
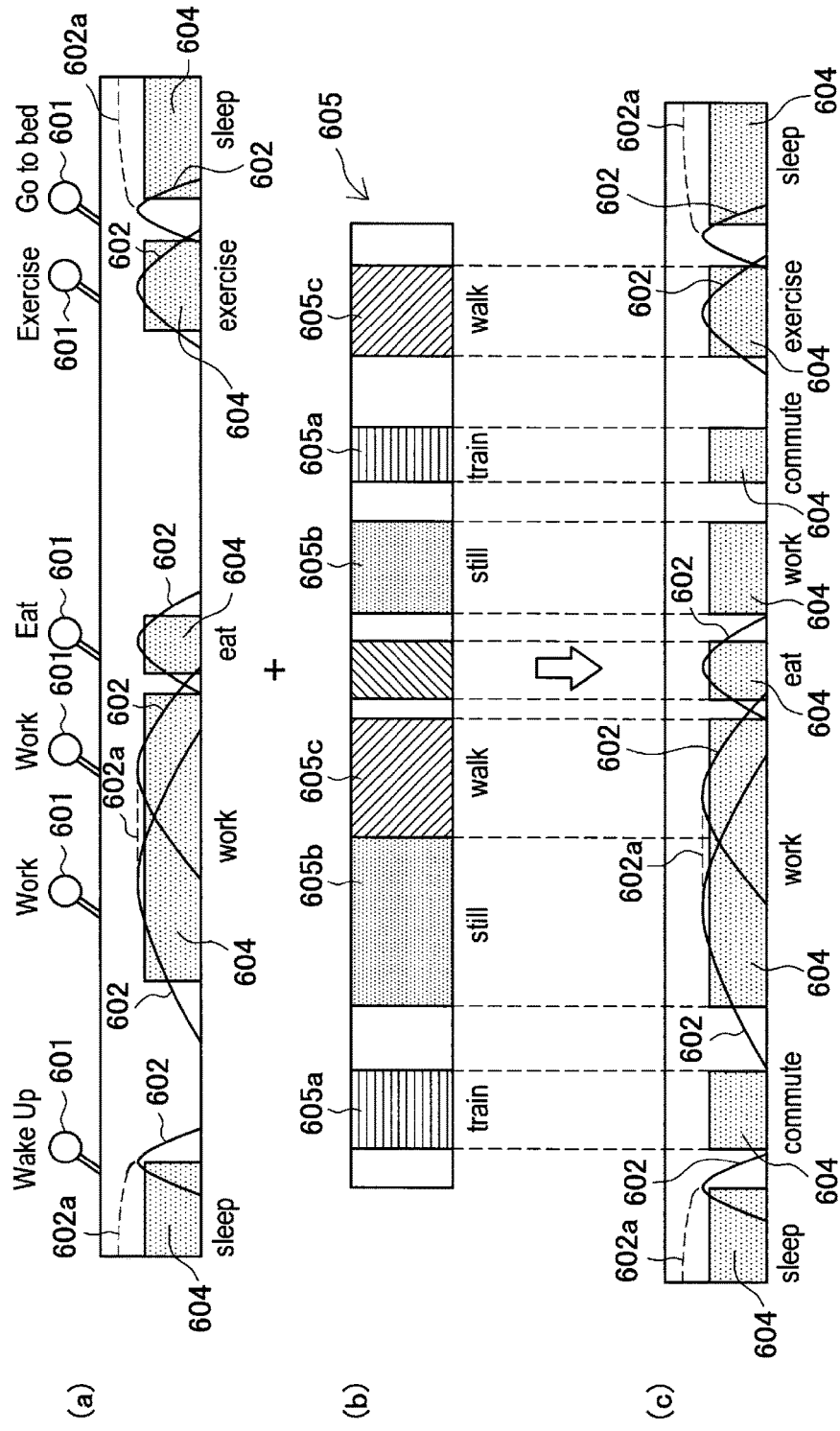
FIG. 5 is a diagram illustrating an example of a behavior analysis unit according to the first embodiment of the disclosure.

FIG. 5 is a diagram illustrating an example of the process of the behavior analysis unit 111 according to the first embodiment of the disclosure.

In the illustrated example, (a) shows a behavior history of the user acquired by the input unit 105. (b) shows a behavior log of the user recognized by the behavior recognition unit 103. (c) shows an integrated log into which information of (a) and (b) is integrated.

The behavior history shown in (a) includes a behavior label 601 input by the user. The behavior label 601 is a label the user assigns to his/her behavior, such as "wake-up," "work," "eat," "exercise," or "go to bed" as illustrated. The behavior analysis unit 111 discretizes information of the behavior label 601 on the time axis. Because the behavior label 601 is information manually input by the user, there is a time band in which no input is present The behavior analysis unit 111 calculates a probability distribution 602 based on the input behavior label 601 in the time band in which no input is present. For example, because a time band in which the user is more likely to eat is around a time when the behavior label 601 of "eat" is input, a probability distribution 602 in which the user's behavior is "eat" is set by specifying the time input to the behavior label 601 as a vertex.

The probability distribution 602 may differ, for example, according to a type of behavior. For example, in the behavior considered to be continued for a comparatively long time such as "work," the probability distribution 602 is comparatively widely distributed around the input time of the behavior label 601. In the behavior considered not to be continued for a long time such as "eat" or "exercise," the probability distribution 602 is comparatively narrowly distributed around the input time of the behavior label 601. In addition, in the behavior that is basically not continuous such as "wake-up" or "go to bed," the probability distribution 602 is more narrowly distributed around the input time of the behavior label 601.

Further, the behavior analysis unit 111 extends the probability distribution 602 on the basis of the anteroposterior relationship of the behavior label 601. For example, if the behavior label 601 of "work" considered to be continued for a comparatively long time has been input twice at relatively close times, the user's behavior "work" is likely to have been continued between the input times. The behavior analysis unit 111 sets a probability distribution 602a indicating that "work" is likely to have been continued between two input times. In addition, a period from an input time of the behavior label 601 of "go to bed" to an input time of the behavior label 601 of "wake up" is a time band of "sleep" in common sense. The behavior analysis unit 111 sets the probability distribution 602a indicating that a time band between "go to bed" and "wake up" is likely to be a "sleep."

As a result of the above, the behavior analysis unit 111 estimates continuous behavior distributions 604 such as "sleep," "work," "eat," and "exercise."

The behavior analysis unit 111 may acquire information indicating that "work is behavior continuous for a comparatively long time," "exercise is behavior not continuous for a long time," or "sleep is likely to be between going to bed and waking up" using the above-described analysis, for example, from the knowledge data 325 indicating a habitual property of a user's behavior reflected in a previous trend of the user's behavior, a general user's behavior, physical limitations, or the like.

A behavior log 605 shown in (b) includes information indicating the user's behavior in each time band such as "movement by train" 605a, "still" 605b, or "walking" 605c. Because the behavior log 605 is information that is automatically acquired, data is basically continuous seamlessly. The behavior analysis unit 111 supplements a behavior history (second behavior information) of the user using the behavior log 605 (first behavior information), and generates an integrated log shown in (c). Here, the behavior analysis unit 111 may also acquire and use the habitual property of the user's behavior reflected in the previous trend of the user's behavior, the general user's behavior, the physical limitations, or the like from the knowledge data 325.

For example, in the illustrated example, it is difficult to estimate when "work" has started and which behavior has been performed between "wake-up" and "work" because there is no input of the behavior label 601 between "wake-up" and "work." Here, referring to the behavior log 605, it can be seen that the behavior log 605a of "movement by train" is recorded in its time band. Here, for example, if there is the knowledge data 325 indicating that movement by train between wake-up and work is likely to be a commute, it is possible to set a behavior distribution 604 of "commute" in its time band.

In addition, in the illustrated example, because an input of the behavior label 601 is absent between "eat" in the afternoon and "exercise" in the late afternoon, it is difficult to estimate behavior in a time band between these. Here, referring to the behavior log 605, it can be seen that the behavior log 605b of "still" and the behavior log 605a of "movement by train" are recorded in its time band. Here, for example, if there is the knowledge data 325 indicating that "work is also likely to be done after lunch if work has been done before lunch" and "movement by train after work in the late afternoon is likely to be a commute," it is possible to set a behavior distribution 604 in which "work" and "commute" subsequent thereto are arranged in its time band.

As described above, the behavior analysis unit 111 generates an integrated log for accurately estimating the user's behavior by combining the behavior log recognized by the behavior recognition algorithm with a behavior history manually input by the user.

For an input of behavior-related information, a method in which the number of inputs is small without performing an input at a specific timing is desirable to reduce an input burden on the user. According to the process of the above-described behavior analysis unit 111, it is possible to estimate the user's behavior by inputting a behavior label at any time when the behavior is being performed even when the user does not necessarily designate a start and end of the behavior. In addition, it is possible to estimate the user's behavior from a previous trend or knowledge data of the user even when the user forgets to input the behavior label and data is missing. Accordingly, because the number of information inputs of the user is reduced, a burden on the user may be reduced.

For example, technology for estimating "work" or "shopping" and high-level behavior of the user such as "work" regardless of manually input information of the user is disclosed in Japanese Patent Application Laid-Open No. 2011-81431 described above. The behavior analysis unit 111 may analyze the user's behavior with the above-described process or using such high-level behavior estimation technology instead.

(1-2-3. Process of Association Analysis Unit)

Next, an example of the process of the association analysis unit 113 according to the first embodiment of the disclosure will be described. The association analysis unit 113 analyzes an association between behavior and a satisfaction degree of the user by analyzing an association between an integrated log generated by the behavior analysis unit 111 or a behavior model and a satisfaction degree log of the user or a log of another service. In the following description, several examples of the process of the association analysis unit 113 according to this embodiment will be described.

(Generation of Ranking of Daily Behavior Pattern)

For example, the association analysis unit 113 generates the ranking of a daily behavior pattern of the user on the basis of a subjective satisfaction degree of the user.

As a first example, the association analysis unit 113 may specify a daily behavior model in which the user's daily satisfaction degree is high as a typical pattern of behavior of which the user's satisfaction degree is high, and specify a daily behavior model in which the user's daily satisfaction degree is low as a typical pattern of behavior of which the user's satisfaction degree is low. The user's daily satisfaction degree may be acquired by presenting a UI for allowing the user to input "Today's satisfaction degree," for example, when the user has set the behavior label 601 of "go to bed."

As a second example, the association analysis unit 113 may specify a behavior model of one day before the user's satisfaction degree in the morning is high as a typical pattern of behavior of which the user's satisfaction degree is high, and specify a behavior model of one day before the user's satisfaction degree in the morning is low as a typical pattern of behavior of which the user's satisfaction degree is low. The user's satisfaction degree in the morning may be acquired by presenting a UI for allowing the user to input a "present satisfaction degree," for example, when the user has set the behavior label 601 of "wake-up," or when the application 230 has been initially started up in one day.

As a third example, the association analysis unit 113 may specify a daily behavior model in which a total or average satisfaction degree of the user is high as a typical pattern of behavior of which the user's satisfaction degree is high, and specify a daily behavior model in which a total or average satisfaction degree of the user is low as a typical pattern of behavior of which the user's satisfaction degree is low. The total or average satisfaction degree of the user may be acquired by presenting a UI for allowing the user to input a "present satisfaction degree" and calculating a total or average satisfaction degree acquired during one day, when the user sets various behavior labels 601.

As described above, the association analysis unit 113 may acquire a daily satisfaction degree of the user and generate the ranking of a daily behavior pattern in various methods. One or combinations of the above-described first to third examples may be adopted.

(Extraction of Relationship Between Specific Behavior and Satisfaction Degree)

In addition, for example, the association analysis unit 113 extracts a relationship between specific behavior of the user and a subjective satisfaction degree of the user.

As a first example, the association analysis unit 113 calculates a satisfaction degree of the user for each time band or day, and specifies a behavior pattern of which a satisfaction degree is included in the top N % (0<N<100) in a certain time band or day as a behavior pattern of which the user's satisfaction degree is high. Here, if the satisfaction degree is calculated for each time band, an average of satisfaction degrees input in the time band may be used as the satisfaction degree of each time band. When the satisfaction degree is calculated daily, a method of acquiring a daily satisfaction degree may be applied as shown in the first to third examples in which the ranking of a daily behavior pattern is generated as the satisfaction degree of each day as described above.

As a second example, the association analysis unit 113 analyzes which behavior has contributed to the satisfaction degree in a time band or day when the user's satisfaction degree is comparatively high. For example, a decision tree analysis technique may be used for the analysis. According to this analysis, the association analysis unit 113 extracts behavior that is estimated to largely contribute to a comparatively high satisfaction degree of the user. This result may indicate, for example, that "the satisfaction degree tends to be high when the user walks for 1 hour."

As a third example, the association analysis unit 113 acquires information on a speech volume and speech content of the user in another service when the user's satisfaction degree is comparatively high, and collects the information as vectors. The association analysis unit 113 extracts a tendency indicating how many times the user has made speech of which content in another service when the satisfaction degree is comparatively high from vectors collected over a period to a certain extent. Thereby, the association analysis unit 113 can extract the user's satisfaction degree from a log of speech of the user in another service. If the user's satisfaction degree can be acquired from the log of the other service, it is possible to recognize the user's satisfaction degrees for more behaviors.

As described above, the association analysis unit 113 may extract a relationship between the user's specific behavior and the user's subjective satisfaction degree by acquiring a satisfaction degree corresponding to the user's behavior in various methods. One or combinations of the above-described first to third examples may be adopted.

Other Examples

The association analysis unit 113 may apply a bias to the satisfaction degree input by the user according to predetermined criteria. An example of the predetermined criteria may be criteria based on information on ambient environmental factors, which are likely to affect the user's mood, such as temperature, humidity, ambient sound, and brightness detected by the sensor 101 or weather, humidity, temperature, earthquake, and the like acquired using service or the like on a network. Thereby, it is possible to reduce an influence of the ambient environments according to a change of the user's satisfaction degree and more purely acquire a value indicating the user's satisfaction degree.

In addition, the association analysis unit 113 may evaluate the satisfaction degree input by the user according to relative evaluation, not absolute evaluation. Thereby, for example, it is possible to evaluate and compare satisfaction degrees of users according to the same criteria between a user whose satisfaction degree change is largely reflected in an input and a user whose satisfaction degree change is not largely reflected in the input. In addition, for example, it is possible to accurately acquire a change of the satisfaction degree of the user such as "bad but improving" or "worse" when a bias is applied to the user's satisfaction degree due to a reason other than behavior such as poor physical condition.

In addition, the association analysis unit 113 may update a behavior pattern specified as a behavior pattern of which the user's satisfaction degree is comparatively high or low according to analysis of a relationship between the behavior and the satisfaction degree of the user thereafter. Thereby, it is possible to acquire a behavior pattern suitable for latest preference of the user by reflecting a change of the user's preference.

Further, the association analysis unit 113 may reflect whether or not a goal set by the user has been achieved in analysis of an association between the behavior and the satisfaction degree. For example, if the user has achieved a goal according to certain behavior, the association analysis unit 113 may further increase and correct the user's satisfaction degree corresponding to the behavior. In this case, it is desirable that the user's goal be a goal of which achievement can be determined by information capable of being acquired by the association analysis unit 113, for example, such as "To decrease the frequency of elevator use," "To walk from the near station to the next station," "To walk X steps or more daily," "To make an amount of activity greater than or equal to Y," or "To take a five minute recess once per hour." The user's goal may not necessarily be set.

The flow of the process according to this embodiment has been described above. The process described here is one example, and other various processes may be executed in this embodiment. For example, processing of input information and a process of generating information to be presented in an example of information input or information presentation to be described below may also be an example of the process to be performed in this embodiment.

(1-3. Example of Information Input)

Subsequently, an example of a UI for acquiring user input information will be described in this embodiment. In the following description, an example in which a UI is displayed on a display having a touch panel will be described. As described above, the input unit 105 of the mobile device 20 may be implemented by various input devices such as a mouse and a keyboard as well as a touch panel. Therefore, UIs corresponding to various input devices that receive an input of the same information as in the following example may be included in the embodiment of the disclosure.

(Inputs of Behavior Label and Satisfaction Degree)

Figure 6:
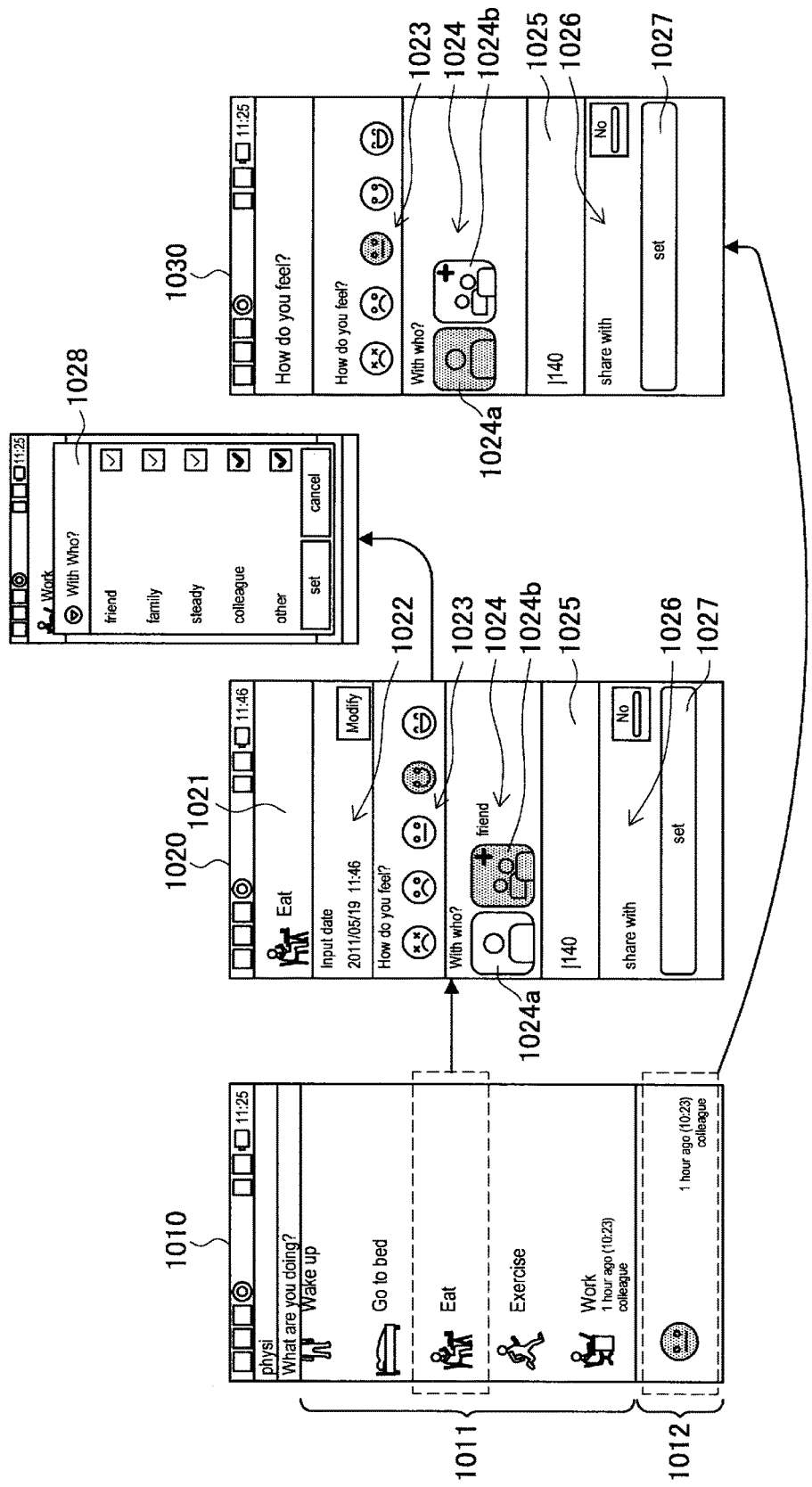
FIG. 6 is a diagram showing an example of a user interface (UI) for allowing a user to input a behavior label and a satisfaction degree in the first embodiment of the disclosure.

FIG. 6 is a diagram showing an example of a UI for allowing the user to input a behavior label and a satisfaction degree in the first embodiment of the disclosure.

In the illustrated example, when the user starts up the application 230 in the mobile device 20, an input menu screen 101 is first displayed. The input menu screen 1010 presents a menu for inputting current or previous behavior of the user or a satisfaction degree in a period including the behavior. The input menu screen 1010 includes behavior label selection indications 1011 and a satisfaction degree indication 1012.

Here, the behavior label selection indications 1011 indicate labels that the user may assign to his/her behaviors as a list. The behavior label selection indications 1011 are displayed, for example, as a list of "wake up," "sleep," "eat,"

"exercise," "work," and the user assigns a behavior label to current or previous behavior by selecting an appropriate behavior label from the list. A plurality of behavior label selection indications 1011 other than those illustrated may be set. In this case, the user searches for a desired behavior label by scrolling the behavior label selection indications 1011. As will be described later, a behavior label arbitrarily added by the user may be added to the behavior label selection indications 1011. In a behavior label selection indication of "work" recently selected by the user among the behavior label selection indications 1011, a selected time "1 hour ago" and companion information "colleague" input at this time may be displayed.

Here, it is desirable to comparatively roughly classify behaviors displayed as the behavior label selection indications 1011 as in an illustrated example. This is because it is easy to analyze a relationship with a satisfaction degree or the like when behavior to which the same behavior label is assigned appears at a certain frequency or more.

In addition, the satisfaction degree indication 1012 indicates a satisfaction degree recently input by the user. In the satisfaction degree indication 1012 as in the recently selected behavior label selection indication 1011, the input time "1 hour ago" and the companion information "colleague" input at this time may be displayed. The user can newly input information on a satisfaction degree by selecting the satisfaction degree indication 1012.

If the user selects one behavior label selection indication 1011 (here "eat") in the input menu screen 1010, a behavior input screen 1020 is displayed. The behavior input screen 1020 includes a behavior label indication 1021, an input time indication 1022, a satisfaction degree input 1023, a companion input 1024, a text input 1025, other service coordination indication 1026, and a set button 1027.

Here, the behavior label indication 1021 indicates a selected behavior label (here "eat") when the behavior input screen 1020 is displayed. The input time indication 1022 indicates a time, which is set as a time when information has been input. The input time indication 1022 is, for example, initially set to a current time, but may be changed by providing a "modify" button. Thereby, the user can input behavior information of a previous time (for example, several hours ago) as well as behavior information at a current time.

The satisfaction degree input 1023 is an indication for inputting a satisfaction degree the user feels at a time indicated by the input time indication 1022 with respect to the behavior indicated by the behavior label indication 1021. The satisfaction degree input 1023 may be displayed, for example, as a UI for selecting an icon indicating a satisfaction degree in a predetermined step. In the illustrated example, five icons each indicating a low satisfaction degree, a slightly low satisfaction degree, an intermediate satisfaction degree, a slightly high satisfaction degree, and a high satisfaction degree are displayed from left to right of the behavior input screen 1020. The user can easily input the satisfaction degree by selecting one of the icons.

The companion input 1024 is an indication for inputting who the user is with at a time indicated by the input time indication 1022 while performing behavior indicated by the behavior label indication 1021. In the illustrated example, the companion input 1024 includes, for example, an icon 1024*a* indicating whether or not there is one person and an icon 1024*b* indicating who the user is with. The user selects the icon 1024*a* in the case of one person. In addition, the user selects the icon 1024*b* when with someone. If the user has selected the icon 1024*b*, a companion selection screen 1028 is displayed. Here, the user selects who the user is with from options of "friend," "family," "colleague," and the like. A result of selection in the companion selection screen 1028 is displayed in the companion input 1024 (here "friend").

The text input 1025 is an indication for freely inputting comments, memos, or the like with respect to the behavior indicated by the behavior label indication 1021. The other service coordination indication 1026 is an indication for setting whether or not to post content or the like input to the text input 1025 on another service, for example, a social service or the like. In the illustrated example, because the other service coordination indication 1026 is set to "No," the content input by the user to the text input 1025 is collected as a behavior log. On the other hand, if the other service coordination indication 1026 is set to "Yes," the content input by the user to the text input 1025 is collected as the behavior log or posted on another service instead.

The set button 1027 is a button for setting content input by the user in the behavior input screen 1020. If the user selects the set button 1027, the content input in the behavior input screen 1020 is acquired as a manually input behavior log or a manually input satisfaction degree log. Among elements displayed on the behavior input screen 1020, the satisfaction degree input 1023, the companion input 1024, and the text input 1025 may not necessarily be input. That is, after the behavior input screen 1020 has been displayed by selecting one behavior label selection indication 1011 of the input menu screen 1010, the set button 1027 may be directly selected. In this case, behavior indicated by the behavior label indication 1021 is acquired as a manually input behavior log of a current time indicated as the input time indication 1022, and other information including a manually input satisfaction degree log is not acquired.

On the other hand, if the user selects the satisfaction degree indication 1012 in the input menu screen 1010, the satisfaction degree input screen 1030 is displayed. The satisfaction degree input screen 1030 includes the satisfaction degree input 1023, the companion input 1024, the text input 1025, the other service coordination indication 1026, and the set button 1027.

At this time, the satisfaction degree input screen 1030 can independently input information on the satisfaction degree at the time without specifying the behavior label. The user selects the set button 1027 by selecting one icon in at least the satisfaction degree input 1023 after the satisfaction degree input screen 1030 has been displayed. The companion input 1024 and the text input 1025 may not necessarily be input. Therefore, at least the manually input satisfaction degree log may be acquired when the satisfaction degree input screen 1030 has been displayed, and further the manually input behavior log may be generated when the companion input 1024 or the text input 1025 has been input.

According to the input UIs of the behavior label and the satisfaction degree as described above, the user can add and input information indicating who the user is with, free comments, or the like in addition to an input of a satisfaction degree along with a label in behavior at the time, and can acquire various information regarding the user's behavior. In addition, the satisfaction degree can be independently input, so that the user can easily input information on the satisfaction degree without having to input all information including the behavior label. In addition, the presence/absence of coordination with another service is selectable, so that an input of information regarding the user's behavior can be easily and directly posted on another service such as a social service.

(Addition of Behavior Label)

Figure 7:
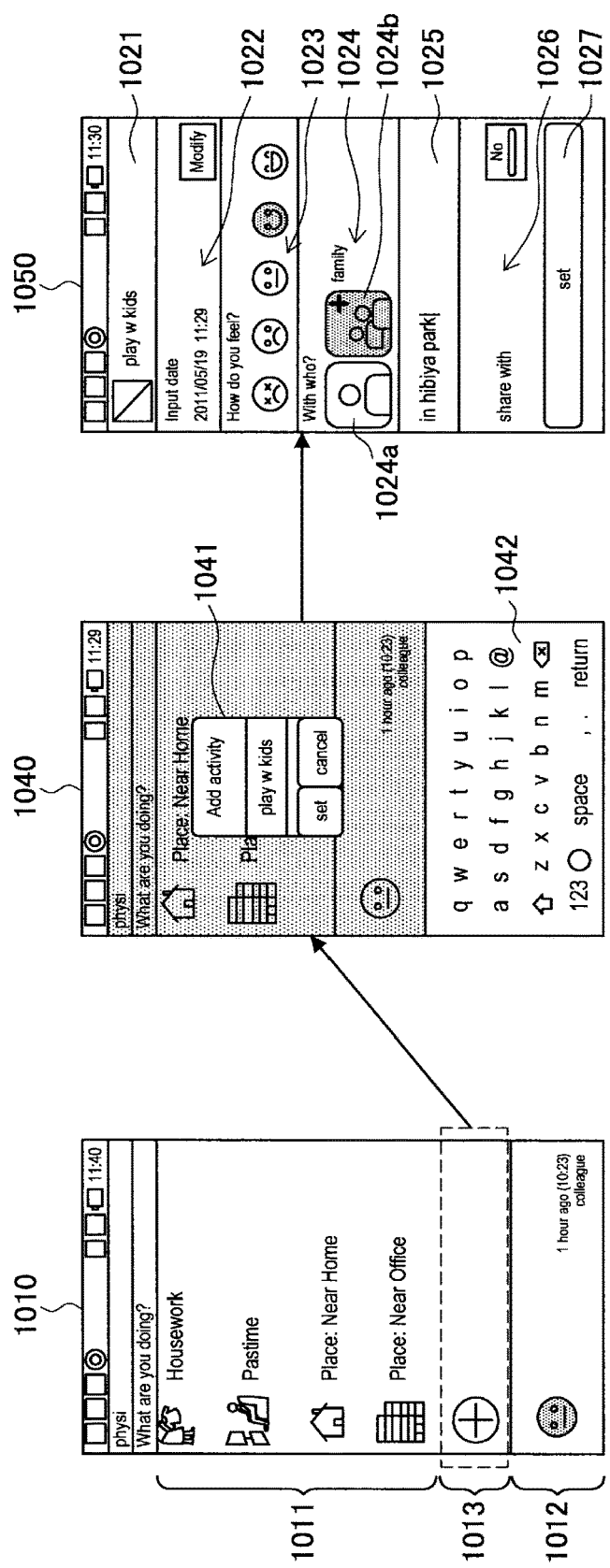
FIG. 7 is a diagram showing an example of a UI for allowing the user to add a behavior label in the first embodiment of the disclosure.

FIG. 7 is a diagram showing an example of a UI for allowing the user to add the behavior label in the first embodiment of the disclosure.

In the illustrated example, a behavior label addition indication 1013 is displayed on the input menu screen 1010. If the user selects the behavior label addition indication 1013, the behavior label addition screen 1040 is displayed. In order to indicate this, the behavior label addition indication 1013 may include, for example, an icon indicating "+" as illustrated, or the like.

The behavior label addition screen 1040 is displayed, for example, to be overlaid on the input menu screen 1010, and includes an input window 1041 and a keyboard 1042. The user inputs a desired behavior name to the input window 1041 using the keyboard 1042. Here, a behavior label name "play with kids" is input.

The behavior label to be added by the user may belong to various attributes. For example, as displayed on the input menu screen 1010 in the illustrated example, various behavior labels such as "Housework," "Pastime," "Place: Near Home," and "Place: Near Office" may be set.

When a new behavior label has been set in the behavior label addition screen 1040, a behavior input screen 1050 may be directly displayed with respect to the new behavior label. Like the above-described behavior input screen 1020, the behavior input screen 1050 may include the behavior label indication 1021, the input time indication 1022, the satisfaction degree input 1023, the companion input 1024, the text input 1025, the other service coordination indication 1026, and the set button 1027.

According to the behavior label addition input UI as described above, it is possible to classify the user's behavior according to a behavior label by adding a behavior label suitable for a personal behavior property or preference of the user, and it is possible to classify behavior further personalized for the user.

(Input of Daily Satisfaction Degree)

Figure 8:
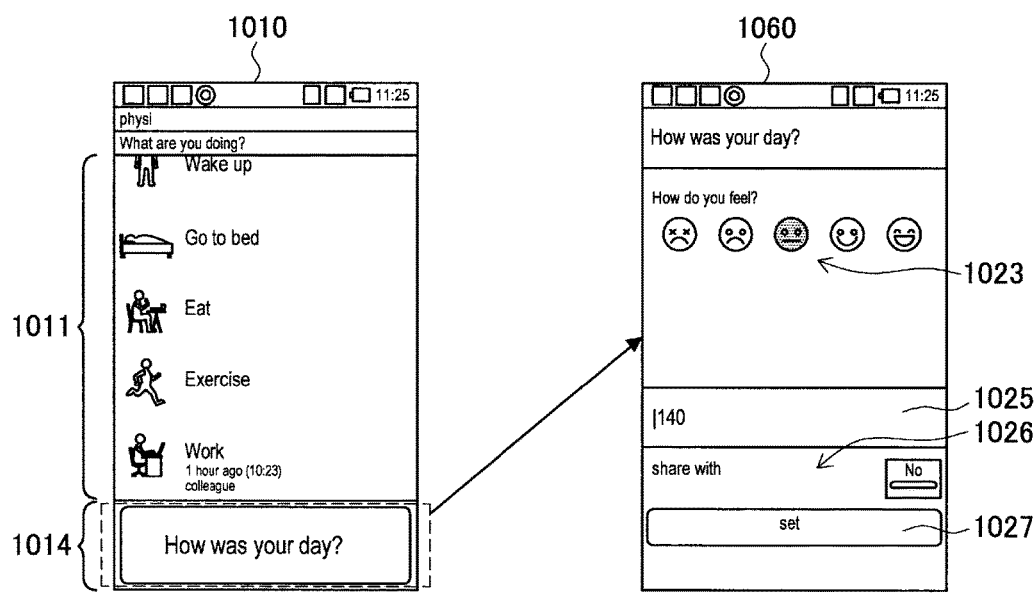
FIG. 8 is a diagram showing an example of a UI for allowing the user to input a daily satisfaction degree in the first embodiment of the disclosure.

FIG. 8 is a diagram showing an example of a UI for allowing the user to input a daily satisfaction degree according to the first embodiment of the disclosure.

In the illustrated example, a daily satisfaction degree input button 1014 is displayed on the input menu screen 1010. If the user selects the daily satisfaction degree input button 1014, a daily satisfaction degree input screen 1060 is displayed.

The daily satisfaction degree input screen 1060 includes the satisfaction degree input 1023, the text input 1025, the other service coordination indication 1026, and the set button 1027. These indication elements are the same as those of the above-described satisfaction degree input screen 1030. However, input information is acquired as a manually input satisfaction degree log that covers the same day, not a specific time.

Here, the daily satisfaction degree input button 1014 may be displayed on the input menu screen 1010, for example, at a specific time such as an average bedtime of the user. In addition, the daily satisfaction degree input screen 1060 may be displayed by selecting the daily satisfaction degree input button 1014, and may also be displayed, for example, after the user selects the behavior label selection indication 1011 of "go to bed," the behavior input screen 1020 of "go to bed" is displayed, and the user's input ends.

According to an input UI of a daily satisfaction degree as described above, if the daily satisfaction degree of the user is used in the process of the above-described association analysis unit 113, information on the daily satisfaction degree can be acquired. In addition, it is possible to induce the user to naturally input the daily satisfaction degree without feeling a burden by devising a display timing of the daily satisfaction degree input button 1014 or the daily satisfaction degree input screen 1060.

(Satisfaction Degree Input According to Plurality of Criteria)

As described with reference to the above-described satisfaction degree input UI 233b, in this embodiment, the user's satisfaction degree may be defined by a plurality of criteria, for example, such as "stress," "refreshment degree," "sleepy," "fatigue," "concentration power," and "mood." Although the user's satisfaction degree has been expressed using one criterion among these in the example of the input UI so far, the user's satisfaction degree may be expressed using a combination of the plurality of criteria. Hereinafter, the case where the user's satisfaction degree is input according to the plurality of criteria will be described with reference to FIGS. 9 to 11.

Figure 9:
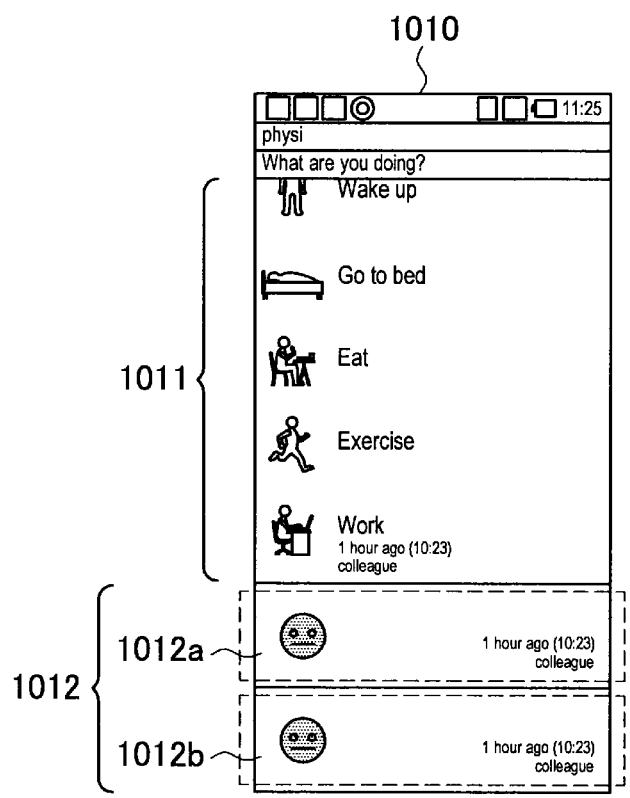
FIG. 9 is a diagram showing a first example of a UI for allowing the user to input a satisfaction degree according to a plurality of criteria in the first embodiment of the disclosure.

FIG. 9 is a diagram showing a first example of a UI for allowing the user to input a satisfaction degree according to a plurality of criteria in the first embodiment of the disclosure.

As described above, in this embodiment, the criteria such as "stress," "refreshment degree," "sleepy," "fatigue," "concentration power," and "mood" can be defined, and the satisfaction degree can be input using the plurality of criteria. In the illustrated example, two of these criteria are used to input the satisfaction degree. Two satisfaction degree indications 1012a and 1012b each corresponding to separate criteria of the satisfaction degree are displayed on the input menu screen 1010.

Here, a screen displayed when the satisfaction degree indications 1012a and 1012b have been selected may be the same screen as the satisfaction degree input screen 1030. The user inputs the satisfaction degree according to the criteria by selecting each of the satisfaction degree indications 1012a and 1012b.

Figure 10:
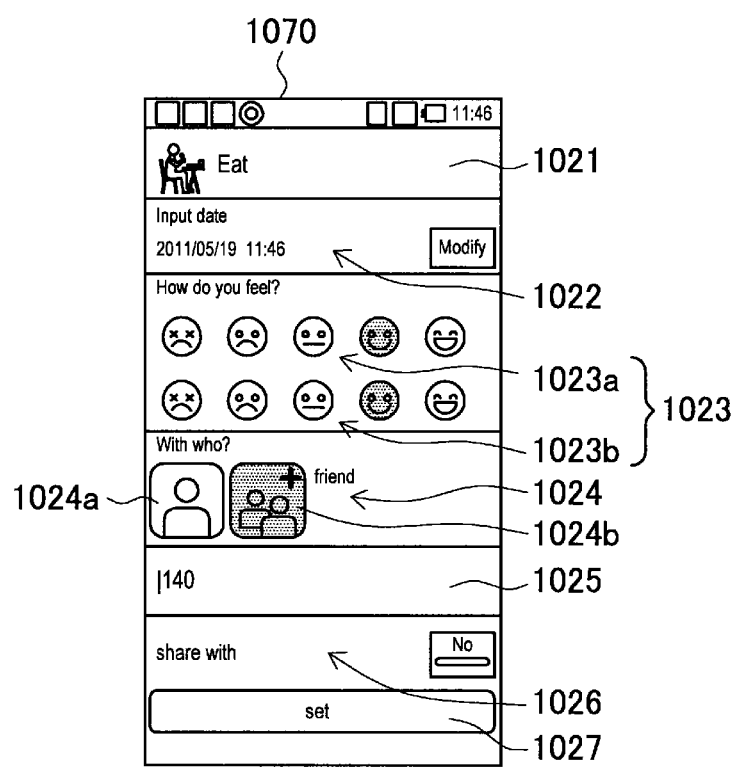
FIG. 10 is a diagram showing a second example of a UI for allowing the user to input a satisfaction degree according to a plurality of criteria in the first embodiment of the disclosure.

FIG. 10 is a diagram showing a second example of a UI for allowing the user to input a satisfaction degree according to a plurality of criteria in the first embodiment of the disclosure.

In the illustrated example, if the user has selected one of the behavior label selection indications 1011 in the input menu screen 1010, a behavior input screen 1070 including two satisfaction degree inputs 1023a and 1023b each corresponding to separate criteria of the satisfaction degree is displayed. The behavior input screen 1070 is the same screen as the above-described behavior input screen 1020, except that the two satisfaction degree inputs 1023a and 1023b are displayed. The user inputs a satisfaction degree according to each criterion by selecting one each from among two sets of icons displayed as the satisfaction degree inputs 1023a and 1023b. In the case of this example, the user selects the satisfaction degree indication 1012 in the menu screen 1010, so that the displayed satisfaction degree input screen 1030 may also equally include the two satisfaction degree inputs 1023a and 1023b.

Figure 11:
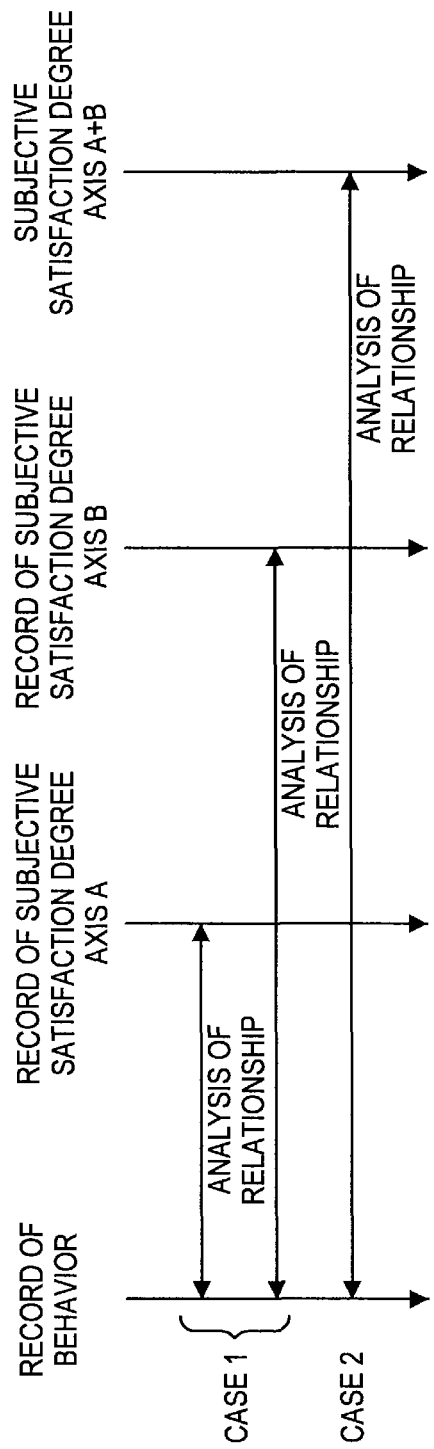
FIG. 11 is a diagram illustrating an example in which a relationship between behavior and a satisfaction degree is analyzed when a plurality of criteria are used in the first embodiment of the disclosure.

FIG. 11 is a diagram illustrating an example in which a relationship between behavior and a satisfaction degree is analyzed when a plurality of criteria are used as in the examples of FIGS. 9 and 10.

In the illustrated example, a subjective satisfaction degree axis A based on a first criterion and a subjective satisfaction degree B based on a second criterion are defined and their satisfaction degrees are recorded. For example, the association analysis unit 113 may analyze a relationship between a "record of behavior" and a "record of the subjective satisfaction degree A" and a relationship between a "record of behavior" and a "record of the subjective satisfaction degree B" as shown in "Case 1" in the drawing. In addition, the association analysis unit 113 may define a "subjective satisfaction degree A+B" obtained by combining the satisfaction degree of the subjective satisfaction degree axis A and the satisfaction degree of the subjective satisfaction degree axis B, and analyze a relationship between the "subjective satisfaction degree A+B" and the "record of behavior" as shown in "Case 2" of the drawing. Although the two criteria of the satisfaction degree have been described in the drawing, three or more criteria of the satisfaction degree may be used.

According to a satisfaction degree input according to the plurality of criteria as described above, it is possible to evaluate the user's satisfaction degree from more various points of view. In addition, a UI of a satisfaction degree input is presented by breaking down it for each criterion, for example, such as "stress" or "happiness," so that the user's input may be facilitated. Although the two criteria of the satisfaction degree have been described in the above-described example, three or more criteria of the satisfaction degree may be used.

(1-4. Example of Information Presentation)

Subsequently, an example of presentation of information for the user according to this embodiment will be described. In the following description, an example in which information is presented to the user according to an image displayed on a display will be described. However, the presentation of information for the user according to the embodiment of the disclosure is not limited to an image using the display of the mobile device 20, and may be, for example, presentation by audio.

(Presentation of Relationship Between Behavior and Satisfaction Degree)

Figure 12:
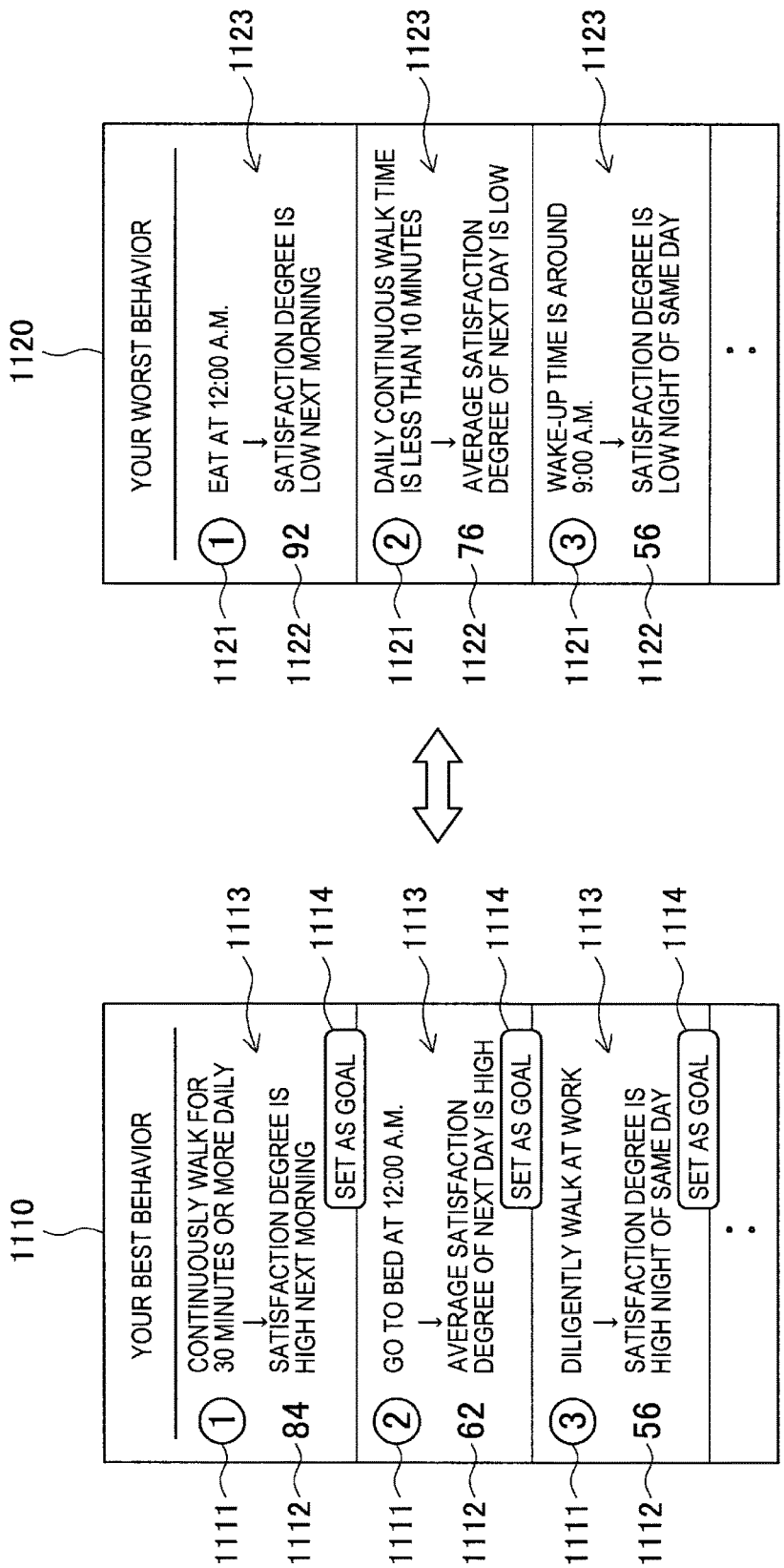
FIG. 12 is a diagram showing an example of a screen on which the relationship between behavior and a satisfaction degree is presented to the user in the first embodiment of the disclosure.

FIG. 12 is a diagram showing an example of a screen on which a relationship between behavior and a satisfaction degree is presented to the user in the first embodiment of the disclosure.

In the illustrated example, behavior, which is estimated to have contributed to a higher satisfaction degree of the user, is presented as a best behavior screen 1110. In addition, behavior, which is estimated to have affected a lower satisfaction degree of the user, is presented as a worst behavior screen 1120. The association analysis unit 113 may estimate this behavior, for example, by decision tree analysis of the relationship between the satisfaction degree and the behavior of the user as described above.

Here, the association analysis unit 113 searches for behavior estimated to have contributed to the satisfaction degree in a time band or a day when the satisfaction degree is higher or lower than a predetermined threshold using a time band of "morning," "night," or the like or a day as a unit. For example, in a day when a satisfaction degree of "morning" is higher than the predetermined threshold, the association analysis unit 113 searches for behavior considered to have contributed to the satisfaction degree from behaviors of a day before the day. In addition, for example, in a day when a satisfaction degree of "night" is lower than the predetermined threshold, the association analysis unit 113 searches for behavior considered to have contributed to the satisfaction degree from behaviors of the day. Further, for example, in a day when a daily average satisfaction degree is higher than the predetermined threshold, the association analysis unit 113 searches for behavior considered to have contributed to the satisfaction degree from behaviors of a day before the day or the day.

A ranking 1111, a score 1112, a cause-effect indication 1113, and a goal button 1114 are displayed on the best behavior screen 1110. The ranking 1111 is attached to behavior in the order in which a relationship between behavior and a satisfaction degree is high. That is, according to the above-described example, the ranking 1111 is assigned in order from behavior of which an association with the satisfaction degree is found to be high from a search result in a relationship between the "satisfaction degree in morning," which is higher than the predetermined threshold, and behavior of a previous day, a relationship between the "satisfaction degree at night," which is higher than the predetermined threshold, and behavior of a current day, and a relationship between the "daily average satisfaction degree," which is higher than the predetermined threshold, and behavior of the previous or current day. The score 1112 is a score of the association. In the cause-effect indication 1113, types of satisfaction degrees of "morning," "night," "daily average," and the like are displayed as the "effects," and the behaviors found by a search are displayed as the "causes."

Accordingly, in the best behavior screen 1110 of the illustrated example, an association of "Satisfaction degree of morning is high" and "Continuously walked for 30 minutes on the previous day" is indicated to be highest. That is, when the user feels a high satisfaction degree in the morning, its cause is likely to be continuous walking for 30 minutes on the previous day. Information presentation for the user according to the best behavior screen 1110 makes the user aware of such a relationship. Further, the user knowing the relationship sets the behavior as a goal by the goal button 1114, so that it is possible to encourage the user to acquire a habit of the behavior in which the user has a high satisfaction degree. Details of setting the behavior as the goal will be described later.

On the other hand, a ranking 1121, a score 1122, and a cause-effect indication 1123 are displayed on the worst behavior screen 1120. These indications are the same as the ranking 1111, the score 1112, and the cause-effect indication 1113 of the best behavior screen 1110, and are displayed in order from behavior of which an association with a satisfaction degree is high among behaviors searched for in satisfaction degrees of "morning," "night," "one day," and the like, which are lower than the predetermined threshold.

Accordingly, in the worst behavior screen 1120 of the illustrated example, an association of "Satisfaction degree of morning is low" and "Ate at 12:00 a.m. on the previous day" is indicated to be highest. That is, when the user only feels a low satisfaction degree in the morning, its cause is likely to be eating at 12:00 a.m., that is, midnight, of the previous day. It is possible to make the user aware of such a relationship and encourage the user to avoid behavior due to a cause of the low satisfaction degree by presenting information to the user according to the worst behavior screen 1120.

(Presentation of Score of Daily Behavior)

Figure 13:
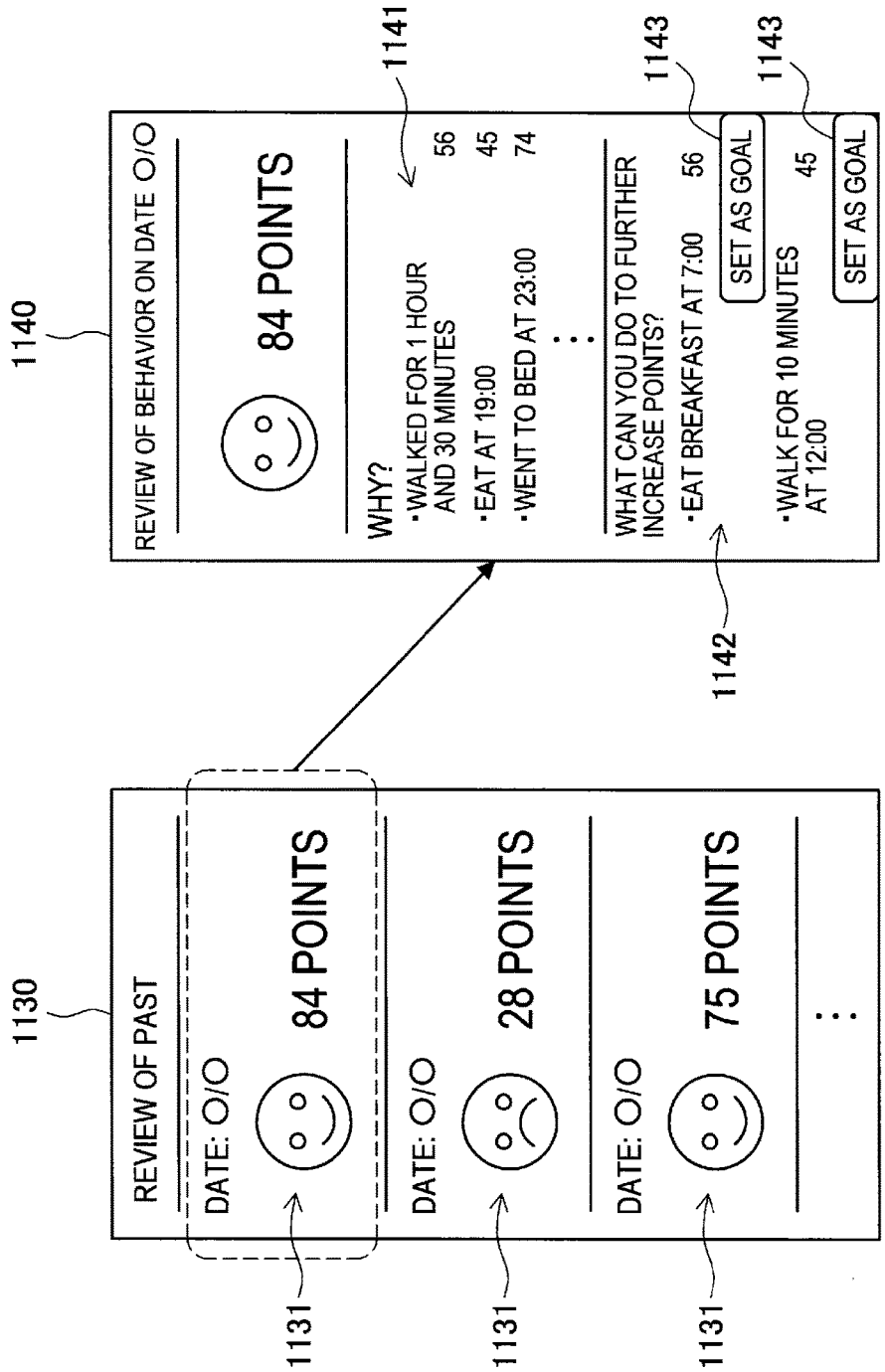
FIG. 13 is a diagram showing an example of a screen on which a daily behavior score is presented to the user in the first embodiment of the disclosure.

FIG. 13 is a diagram showing an example of a screen on which a daily behavior score is presented to the user in the first embodiment of the disclosure.

In the illustrated example, a daily behavior score history is presented as a score history screen 1130. A behavior score indication 1131 of a previous day is displayed on the score history screen 1130. As illustrated, the score indication 1131 may include an icon indicating a score level in addition to a date and a score. A score indicated as the score indication 1131 may indicate how much the user has practiced behavior to increase the satisfaction degree in the same day from a relationship between the previous behavior and the satisfaction degree of the user.

If the user selects the score indication 1131 of one day in the score history screen 1130, a behavior score screen 1140 of the day is displayed. In addition to the date, the score and the icon, a practiced behavior indication 1141, a recommended behavior indication 1142, and a goal button 1143 are displayed on the behavior score screen 1140.

Here, the practiced behavior indication 1141 indicates behavior of which a satisfaction degree is estimated to be high from a relationship between previous behavior and a satisfaction degree among the user's behaviors of the day. A score indicated along with content of behavior indicates an association between behavior and a higher satisfaction degree of one day. That is, in the illustrated example, a daily behavior score is indicated to be "84" as a result of behavior "Walking for 1 hour and 30 minutes daily," which is estimated to have an association of "56" with a higher satisfaction degree of one day, behavior "Eating at 19:00," which is estimated to have an association of "45," behavior "Going to bed at 23:00," which is estimated to have an association of "74," and the like.

Further, a recommended behavior indication 1142 indicates behavior estimated to increase a future satisfaction degree from a relationship between previous behavior and a satisfaction degree, among behaviors the user has not performed in the same day. Like the above-described indication 1141, a score indicated along with content of behavior indicates an association between the behavior and a higher satisfaction degree of one day.

As described above, it is possible to provide an opportunity for the user to review his/her behavior by presenting evaluation of daily behavior of the user based on a relationship between the behavior and the satisfaction degree of the user. In addition, it is possible to provide the user with a hint of behavior for further increasing the satisfaction degree by the recommended behavior indication 1142. Further, it is possible to encourage the user to further increase the satisfaction degree according to behavior by setting the behavior as a goal by the goal button 1143. Details of setting the behavior as the goal will be described later.

(Presentation of Behavior Pattern)

Figure 14:
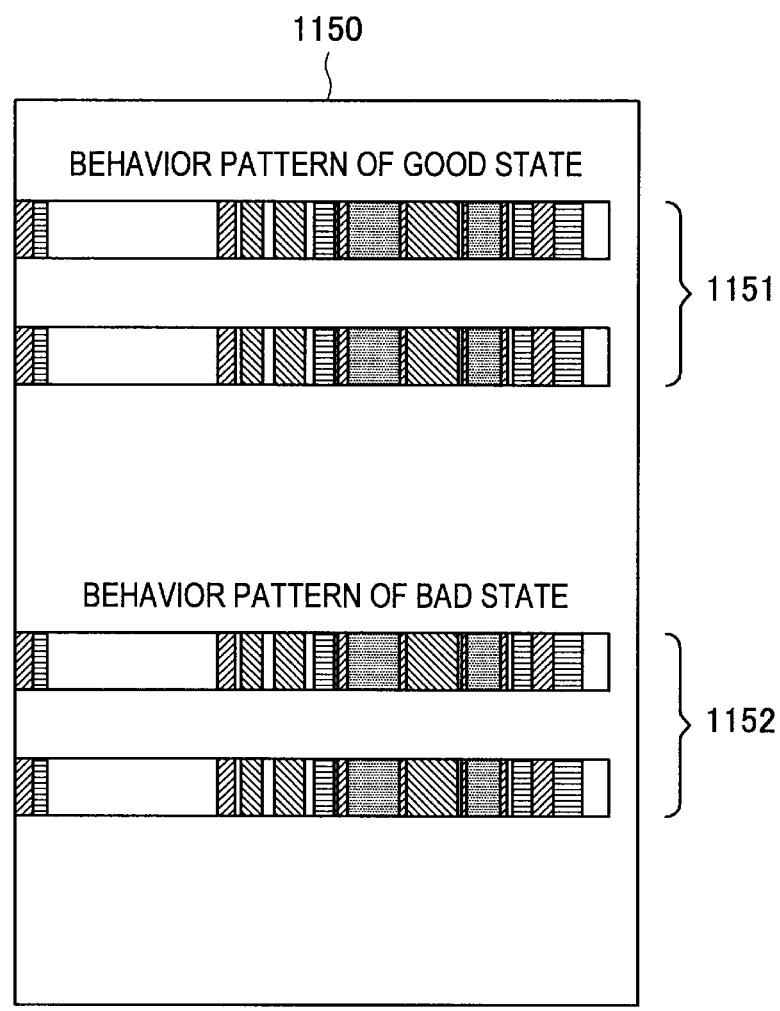
FIG. 14 is a diagram showing an example of a screen on which a behavior pattern is presented to the user in the first embodiment of the disclosure.

FIG. 14 is a diagram showing an example of a screen on which a behavior pattern is presented to the user in the first embodiment of the disclosure.

In the illustrated example, a behavior model of a day when the user's satisfaction degree is comparatively high is displayed as a behavior pattern indication 1151 indicating "a behavior pattern of a good state" on a behavior pattern presentation screen 1150. In addition, a behavior model of a day when the user's satisfaction degree is comparatively low is displayed as a behavior pattern indication 1152 indicating "a behavior pattern of a bad state."

As described above, it is possible to make the user aware of a relationship between his/her behavior pattern and a satisfaction degree and help the user obtain a hint for improving behavior so as to increase the satisfaction degree by presenting a behavior pattern of a day when the satisfaction degree is comparatively high or low to the user. It is possible to easily practice behavior that increases the satisfaction degree by presenting the behavior pattern and making the user reflect, for example, "the behavior pattern of the good state" in a daily behavior plan.

(Presentation of Ideal Behavior for User)

Figure 15:
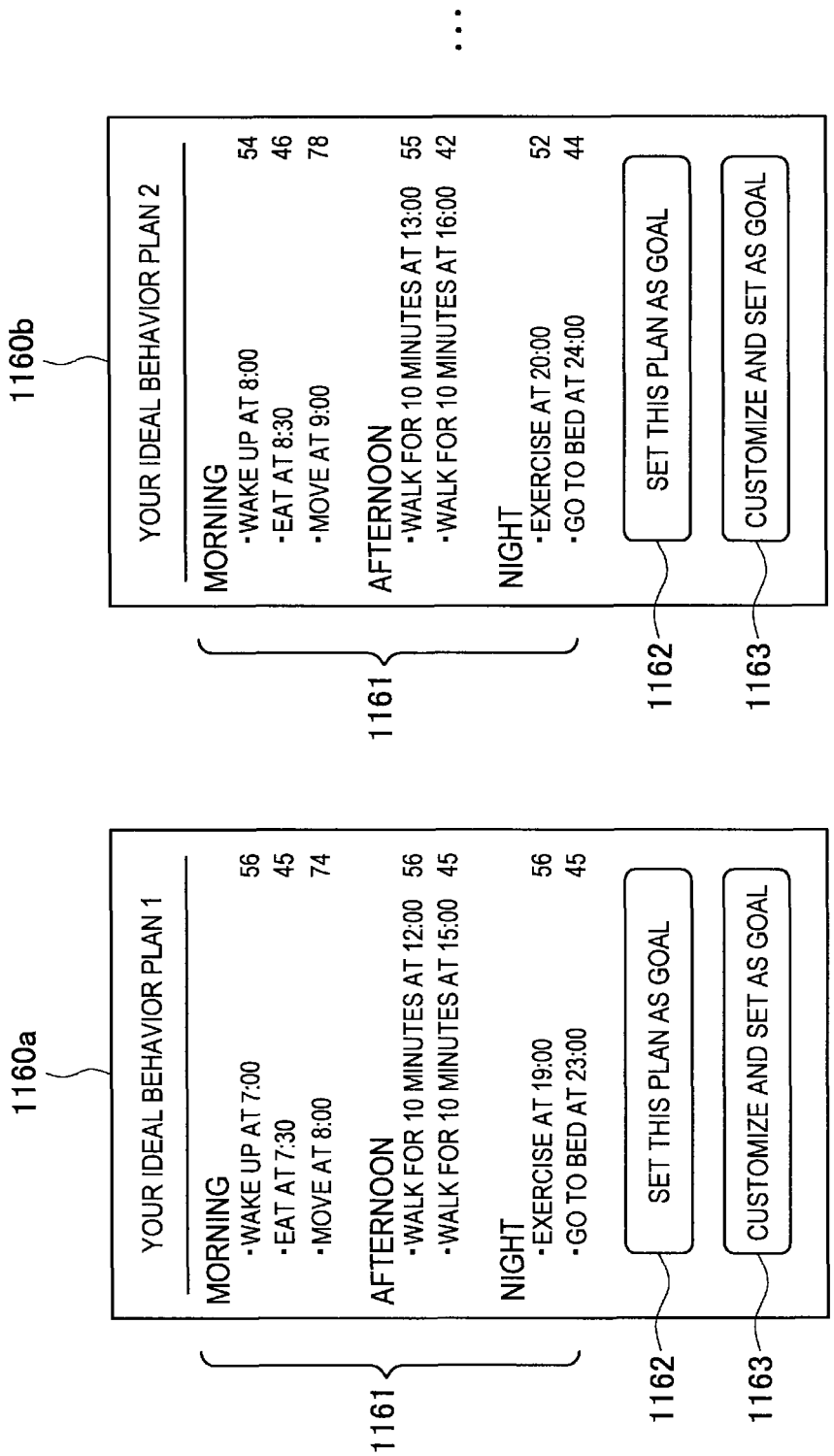
FIG. 15 is a diagram showing an example of a screen on which ideal behavior for the user is presented in the first embodiment of the disclosure.

FIG. 15 is a diagram showing an example of a screen on which ideal behavior for the user is presented in the first embodiment of the disclosure.

In the illustrated example, the ideal behavior for the user is presented as an ideal behavior screen 1160. An ideal behavior indication 1161, a goal button 1162, and a customize/goal button 1163 are displayed on the ideal behavior screen 1160. Like ideal behavior screens 1160*a*, 1160*b*, . . . , a plurality of pattern ideal behavior screens may be displayed.

The ideal behavior indication 1161 is a daily behavior plan assembled with behavior that increases the satisfaction degree of the user estimated from a relationship between previous behavior and a satisfaction degree of the user. The score displayed along with the behavior indicates an association between the behavior and a higher satisfaction degree of one day. For example, as illustrated, the ideal behavior indication 1161 may be displayed in text by dividing it into "morning," "afternoon," and "night," and displayed in a graph as in an example shown in FIG. 14. For the behavior displayed as the ideal behavior indication 1161, behavior estimated to increase the satisfaction degree of the user is assembled, for example, on the basis of conditions of variations of a wake-up time (7:00, 8:00, or the like), a business day, a holiday, and the like. To generate ideal behavior, a previous behavior history or behavior knowledge data of the user, for example, for start and end times of work of the user, a day when the user works, and a general eating time, may be used.

The user can set the behavior plan as a goal of the same day by selecting an ideal behavior screen 1160 indicating a desired ideal behavior plan, for example, from among a plurality of displayed ideal behavior screens 1160*a*, 1160*b*, . . . , and selecting the goal button 1162. In addition, when there is no desired one among presented behavior plans, the user corrects the presented ideal behavior plan and sets the corrected plan as a goal of the same day by selecting the customize/goal button 1163. Details of setting behavior as a goal will be described later in detail.

As described above, it is possible to help the user plan daily behavior and induce the user to select behavior of a higher satisfaction degree by presenting an ideal behavior plan to the user. In addition, it is possible to set an ideal behavior plan considering an influence on daily behavior as the user's goal according to a random element of a mood of the same day of the user or whether or not work is busy.

(Presentation of Goal of Behavior of User)

Figure 16:
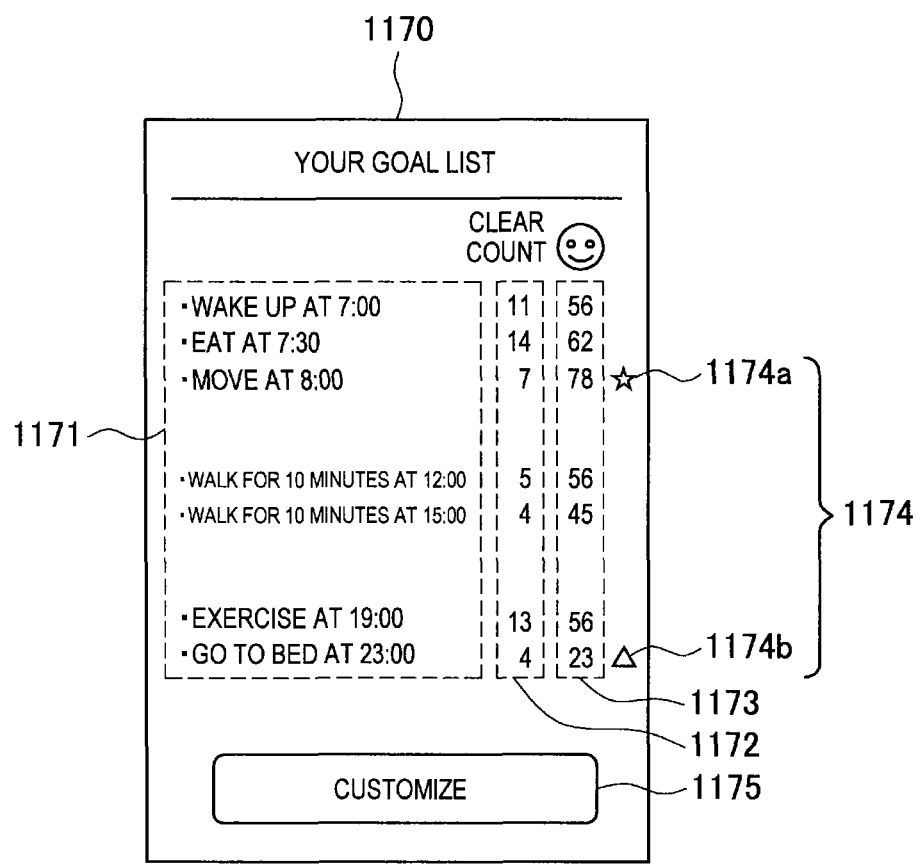
FIG. 16 is a diagram showing an example of a screen on which a goal of behavior of the user is presented in the first embodiment of the disclosure.

FIG. 16 is a diagram showing an example of a screen on which a goal of behavior of the user is presented in the first embodiment of the disclosure.

In the illustrated example, the goal of the behavior of the user is presented as a goal behavior screen 1170. On the goal behavior screen 1170, a goal behavior indication 1171, a goal clear count indication 1172, a goal behavior score 1173, a good/bad goal mark 1174, and a customize button 1175 are displayed.

Here, the user sets behavior shown as the goal behavior indication 1171 as a goal. As shown in the above-described example, the user can set specific behavior during one day as the goal, for example, such as "Wake up at 7:00" or "Go to bed at 23:00," in the best behavior screen 1110, the behavior score screen 1140, the ideal behavior screen 1160, and the like. In addition, the user may freely set the goal on a screen for setting the goal as well as the above-described screens.

The goal clear count indication 1172 indicates the number of times that the user has achieved goal behavior shown as the goal behavior indication 1171 in actual behavior. In addition, when the goal has been achieved, that is, when its behavior has been practiced, the goal behavior score 1173 indicates how much the behavior has contributed to a higher satisfaction degree of the user. A good goal mark 1174a is displayed for goal behavior of which the goal behavior score 1173 is highest, and a bad goal mark 1174b is displayed for goal behavior of which the goal behavior score 1173 is lowest.

A goal for which the good goal mark 1174a has been displayed, here "Move at 8:00," indicates behavior the user sets as the goal, and indicates behavior of which the satisfaction degree is likely to be high when the goal has been achieved. This goal is a "good goal" capable of further increasing the satisfaction degree by the user's behavior while the user achieves the goal. In this goal, behavior ideal for the user is considered to be consistent with behavior in which the user actually obtains the satisfaction degree.

On the other hand, a goal for which the bad goal mark 1174b has been displayed, here "Go to bed at 23:00," indicates behavior the user sets as the goal, and indicates behavior of which the satisfaction degree is less likely to be high when the goal has been achieved. This goal is a "bad goal" in which it is difficult to increase the satisfaction degree according to the user's behavior even when the user's goal is achieved. In this goal, behavior ideal for the user is considered to be different from behavior in which the user actually obtains the satisfaction degree. For example, because "Go to bed at 23:00" is not suitable for the user's life rhythm even when the user's ideal is "Go to bed early" according to an example of "Go to bed at 23:00," the satisfaction degree may be low due to long yet shallow sleep.

Although an example in which the user sets behavior as a goal has been described above, this embodiment of the disclosure is not limited thereto. The user's goal may be a goal capable of being achieved as a result of behavior, for example, such as daily calorie consumption or activity amount. In this case, as in the above-described example, the goal may also be evaluated by a clear count of the goal, a score of the satisfaction degree when the goal is achieved, or the like.

Figure 17:
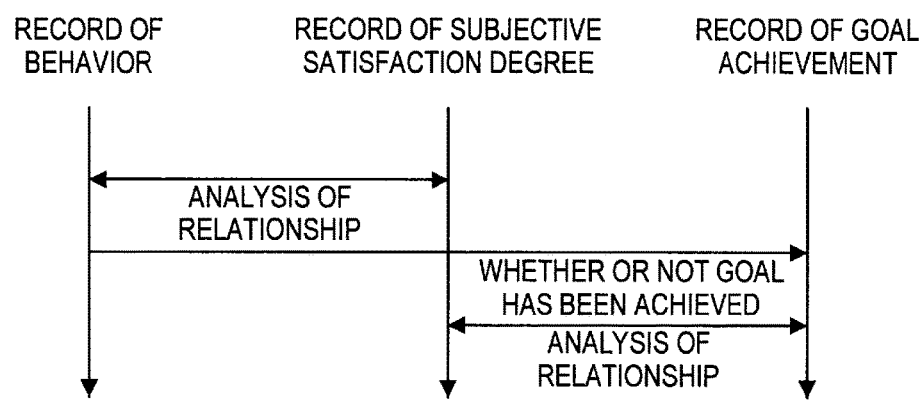
FIG. 17 is a diagram illustrating an example of relationships between behavior, a satisfaction degree, and a goal in the first embodiment of the disclosure.

FIG. 17 is a diagram illustrating an example of relationships between behavior, a satisfaction degree, and a goal in the first embodiment of the disclosure.

In this embodiment, a record of behavior, a record of a subjective satisfaction degree of the user, and a record of whether or not the user has achieved a goal may be recorded independently of each other. Accordingly, the goal can be set independently of the behavior or the satisfaction degree. However, the goal of which achievement can be determined from a record of behavior is, for example, specific behavior or calorie consumption by behavior.

As illustrated, the association analysis unit 113 analyzes an association between behavior and a satisfaction degree from a record of behavior and a record of a satisfaction degree, and also determines whether or not the goal has been achieved from a record of behavior. Further, the association analysis unit 113 analyzes the satisfaction degree when the goal has been achieved, and presents information as shown in the above-described goal behavior screen 1170 to the user.

As described above, it is possible to present whether or not behavior the user sets as the goal contributes to increasing the satisfaction degree of the user and provide an opportunity to self-examine, for example, "whether or not an unreasonable goal is set," by presenting a behavior goal and its evaluation to the user. It is possible to know which goal is suitable for the user.

(Presentation of Behavior Patterns of Other Users)

Figure 18:
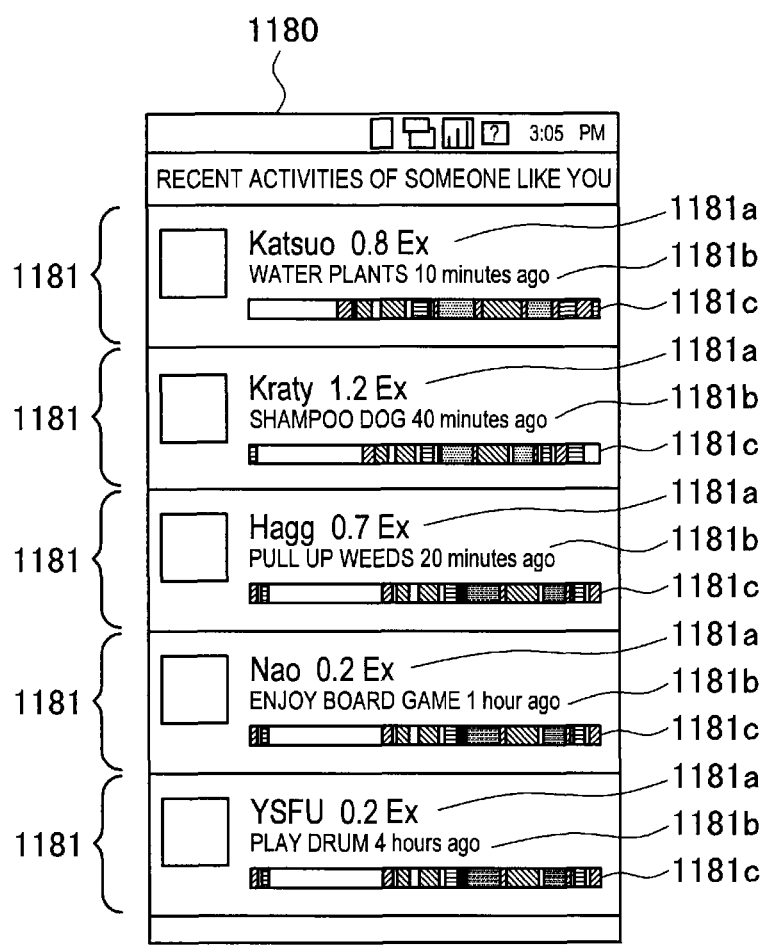
FIG. 18 is a diagram showing an example of a screen on which behavior patterns of other users are presented in the first embodiment of the disclosure.

FIG. 18 is a diagram showing an example of a screen on which behavior patterns of other users are presented in the first embodiment of the disclosure.

In the illustrated example, the behavior patterns of the other users each having an association with a behavior pattern of the user are presented as an other user behavior pattern screen 1180. The other user behavior pattern screen 1180 includes one or more other user behavior pattern indications 1181. Each other user behavior pattern indication 1181 includes an activity amount indication 1181a, a recent activity indication 1181b, and a behavior pattern indication 1181c.

Here, other users displayed on the other user behavior pattern screen 1180 may be extracted as other users (1) similar to the user generally in a relationship between the behavior pattern and the satisfaction degree, (2) similar to the user in a behavior pattern when the satisfaction degree is high or low, (3) similar to the user in the behavior pattern when the satisfaction degree is high and different from the user in the behavior pattern when the satisfaction degree is low, or vice versa, and (4) similar to the user in the behavior pattern but different from the user in a relationship between the behavior pattern and the satisfaction degree.

In addition, the other users displayed on the other user behavior pattern screen 1180 may be arbitrarily designated by the user. In this case, the user can designate friends and the like as the displayed other users. In addition, the user may designate a user satisfying a condition regarding behavior such as a user who walks for 1 hour or more or a user having the same sex or age as him/her, and display the users on the other user behavior pattern screen 1180. Further, the user may follow, for example, a user he/she wants to refer to, among the users displayed on the other user behavior pattern screen 1180, and then continuously make the other user behavior pattern screen 1180 display a behavior pattern of the user.

As described above, the behavior patterns of the other users are presented, so that the user can sympathize with other users having similarities by finding the other users similar to him/her, or can refer to other users by finding the other users having senses different from him/her. In this embodiment, this function may be obtained by information regarding a behavior pattern of the user presented on the basis of a personal feeling of the user reflected in the satisfaction degree.

(Behavior Recommendation and UI for Feedback)

Figure 19:
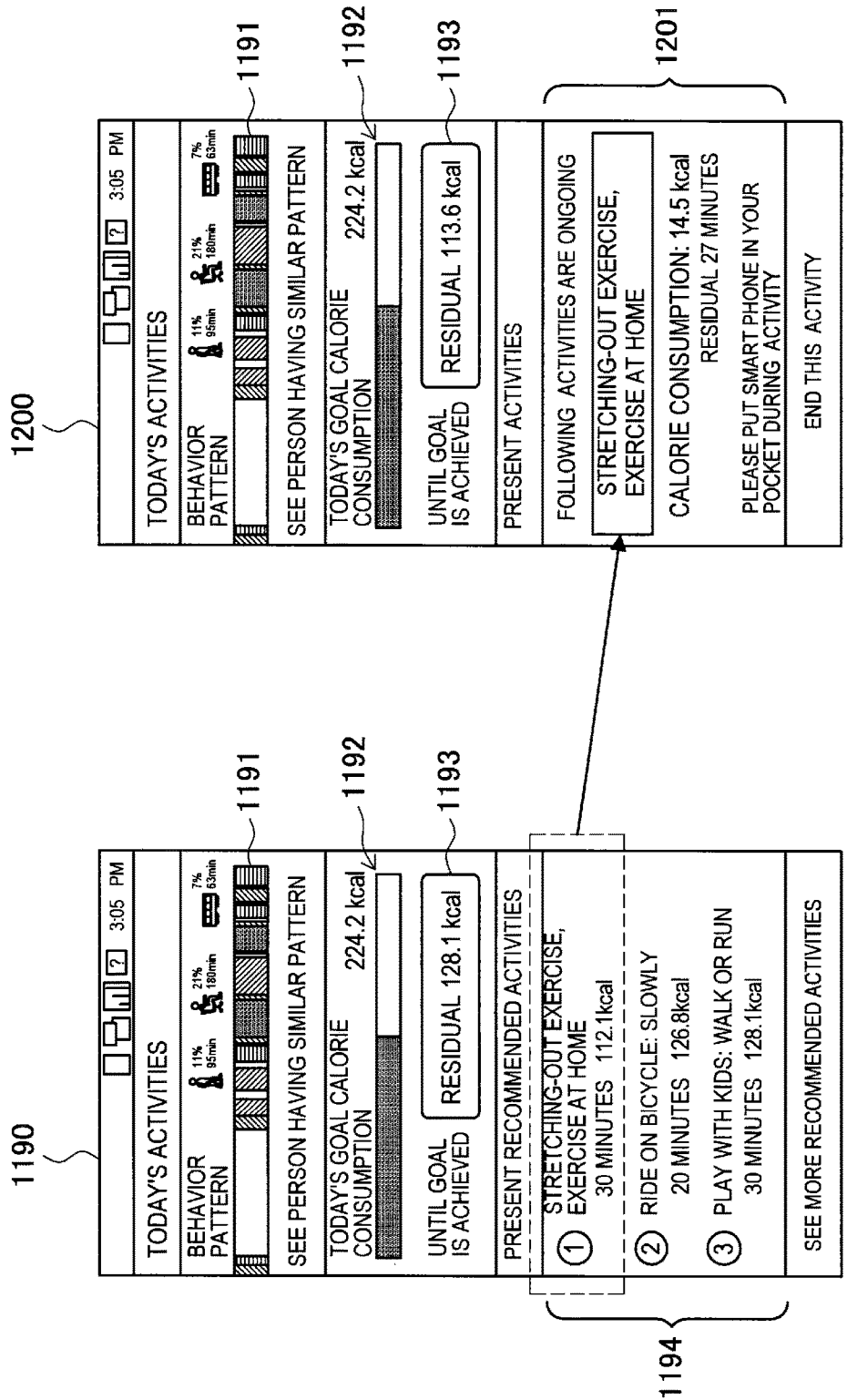
FIG. 19 is a diagram showing an example of a UI for presenting recommended behavior to the user and further acquiring feedback for the presentation in the first embodiment of the disclosure.

FIG. 19 is a diagram showing an example of a UI for presenting recommended behavior and further acquiring feedback for the presentation in the first embodiment of the disclosure.

In the illustrated example, a behavior pattern indication 1191, a calorie consumption indication 1192, a residual calorie indication 1193, and a recommended behavior indication 1194 are displayed on a behavior information screen 1190 that presents information regarding behavior to the user. The behavior pattern indication 1191 indicates a behavior pattern of the user of the same day estimated from behaviors so far in one day. The calorie consumption indication 1192 indicates calorie consumption of the user of the same day calculated from an activity amount of the user recognized by the behavior recognition unit 103. When the user sets a goal value of the calorie consumption, the residual calorie indication 1193 indicates the residual calories up to the goal calorie consumption of the same day.

The recommended behavior indication 1194 is a list of behaviors recommended for the user at this time. Information on recommended behaviors indicated by the recommended behavior indication 1194 is generated by the presentation information generation unit 115. The presentation information generation unit 115 selects behavior that increases the satisfaction degree of the user as recommended behavior, for example, using an association between the behavior and the satisfaction degree of the user analyzed by the association analysis unit 113. In addition, the presentation information generation unit 115 selects desirable behavior for the user to achieve the above-described calorie consumption goal, a goal of specific behavior, and the like as recommended behavior. Here, the user's goal is not limited to a goal to be achieved for one day, and may be a goal to be achieved in a period such as one week.

Further, the presentation information generation unit 115 may select recommended behavior in consideration of a current position or behavior of the user, a time band, and the like. For example, the presentation information generation unit 115 may recommend behavior such as "Stand up" if a result of analysis by the behavior analysis unit 111 indicates that the user is moving by train, or recommend behavior such as "Walk home" if the user arrives at a near station when coming home. In addition, the duration of behavior and calorie consumption may be displayed on the recommended behavior indication 1194.

The user refers to the recommended behavior indication 1194 presented as described above as behavior reference information. At this time, the behavior pattern indication 1191, the calorie consumption indication 1192, and the residual calorie indication 1193 are displayed, so that the user can obtain a hint suitable to determine behavior from these.

Here, if the user selects one of recommended behaviors displayed as the recommended behavior indication 1194, a behavior screen 1200 is displayed. On the behavior screen 1200, a behavior indication 1201 of behavior (activity) selected by the user is displayed instead of the recommended behavior indication 1194 of the behavior information screen 1190. The user executes activity by carrying the mobile device 20, thereby causing the behavior recognition unit 103 to recognize an activity amount and detect calorie consumption by the activity in real time.

The selection of the recommended behavior indication 1194 by the user is transmitted from the input unit 105 of the mobile device to the server device 30 as feedback information indicating which behavior has been selected by the user among a plurality of presented recommended behaviors. The association analysis unit 113 or the presentation information generation unit 115 uses the information, for example, as the user's preference and criteria for selecting recommended behavior in the future.

In the behavior information screen 1190, if no desired behavior is indicated by the recommended behavior indication 1194, the user can cause other recommended behaviors to be displayed by selecting "See more recommended activities." In addition, when selected activity is stopped in the behavior screen 1200, the user can return to the behavior information screen 1190 by selecting "End this activity." Here, information indicating that "the user has requested presentation of behaviors other than initially displayed recommended behaviors" or that "the user has stopped the activity" may also be transmitted from the input unit 105 to the server device 30 as information indicating the user's preference, and used by the association analysis unit 113 or the presentation information generation unit 115.

As described above, it is possible to present reference information suitable for the user to select behavior, for example, in terms of goal achievement, satisfaction-degree improvement, and preference of the user. In addition, feedback of the user for the presented recommended behaviors is acquired as information, so that behavior presented as recommended behavior can be corrected, for example, to be suitable for the user's preference.

2. Second Embodiment

Next, the second embodiment of the disclosure will be described. Although a device for implementing the functions is different between this embodiment and the first embodiment, the functions are identical. Accordingly, differences will be described with reference to FIG. 20 in the following description, and detailed description of the functions is omitted. Examples of a process flow, an information input, and information presentation are also similar.

FIG. 20 is a block diagram showing a functional configuration of an information processing system according to the second embodiment of the disclosure. An information processing system 60 includes a mobile device 70. The mobile device 70 includes the sensor 101, the behavior recognition unit 103, the input unit 105, the other service information acquisition unit 107, the output unit 117, the information acquisition unit 109, the behavior analysis unit 111, the association analysis unit 113, and the presentation information generation unit 115.

These functions are the same as those implemented by the mobile device 20 and the server device 30 in the above-described first embodiment. However, in this embodiment, the information acquisition unit 109, the behavior analysis unit 111, the association analysis unit 113, and the presentation information generation unit 115 are implemented by a CPU, a RAM, a ROM, and the like in the mobile device 70. The information acquisition unit 109 has an internal interface function of the mobile device 70, and acquires information from the behavior recognition unit 103, the input unit 105, and the other service information acquisition unit 107. The output unit 117 presents information acquired from the presentation information generation unit 115 via the internal interface of the mobile device 70 to the user.

As described above, in this embodiment, the functions of the information processing system 60 are implemented by the mobile device 70. Thereby, the user can receive presentation of information regarding behavior even when he/she does not necessarily perform communication via a network.

3. Hardware Configuration

Next, a hardware configuration of the information processing apparatus 900 which may realize mobile device 20, 70 and server device 30 according to the embodiments of the present disclosure described above will be described in detail with reference to FIG. 21.

FIG. 21 is a block diagram for describing a hardware configuration of the information processing apparatus 900 according to an embodiment of the present disclosure.

The information processing apparatus 900 includes a CPU 901, a ROM 903, and a RAM 905. Furthermore, the information processing apparatus 900 may also include a host bus 907, a bridge 909, and external bus 911, an interface 913, an input device 915, an output device 917, a storage device 919, a drive 921, a connection port 923, and a communication device 925.

The CPU 901 functions as a processing device and a control device, and controls the overall operation or a part of the operation of the information processing apparatus 900 according to various programs recorded in the ROM 903, the RAM 905, the storage device 919 or a removable recording medium 927. The ROM 903 stores programs to be used by the CPU 901, processing parameters and the like. The RAM 905 temporarily stores programs to be used in the execution of the CPU 901, parameters that vary in the execution, and the like. The CPU 901, the ROM 903 and the RAM 905 are connected to one another through the host bus 907 configured by an internal bus such as a CPU bus. The host bus 907 is connected to the external bus 911 such as a PCI (Peripheral Component Interconnect/Interface) bus via the bridge 909.

The input device 915 is input means to be operated by a user, such as a mouse, a keyboard, a touch panel, a button, a switch, a lever or the like. Further, the input device 915 may be remote control means that uses an infrared or another radio wave, or it may be an external connection device 929 such as a mobile phone, a PDA or the like conforming to the operation of the information processing apparatus 900. Furthermore, the input device 915 is configured from an input control circuit or the like for generating an input signal based on information input by a user with the operation means described above and outputting the signal to the CPU 901. A user of the information processing apparatus 900 can input various kinds of data to the information processing apparatus 900 or instruct the information processing apparatus 900 to perform processing, by operating the input device 915.

The output device 917 is configured from a device that is capable of visually or auditorily notifying a user of acquired information. Examples of such device include a display device such as a CRT display device, a liquid crystal display device, a plasma display device, an EL display device or a lamp, an audio output device such as a speaker or a headphone, a printer, a mobile phone, a facsimile and the like. The output device 917 outputs results obtained by various processes performed by the information processing apparatus 900, for example. To be specific, the display device displays, in the form of text or image, results obtained by various processes performed by the information processing apparatus 900. On the other hand, the audio output device converts an audio signal such as reproduced audio data or acoustic data into an analogue signal, and outputs the analogue signal.

The storage device 919 is a device for storing data configured as an example of a storage unit of the information processing apparatus 900. The storage device 919 is configured from, for example, a magnetic storage device such as a HDD (Hard Disk Drive), a semiconductor storage device, an optical storage device, or a magneto-optical storage device. This storage device 919 stores programs to be executed by the CPU 901, various types of data, and various types of data obtained from the outside, for example.

The drive 921 is a reader/writer for a recording medium, and is incorporated in or attached externally to the information processing apparatus 900. The drive 921 reads information recorded in the attached removable recording medium 927 such as a magnetic disk, an optical disk, a magneto-optical disk, or a semiconductor memory, and outputs the information to the RAM 905. Furthermore, the drive 921 can write in the attached removable recording medium 927 such as a magnetic disk, an optical disk, a magneto-optical disk, or a semiconductor memory. The removable recording medium 927 is, for example, a DVD medium, an HD-DVD medium, or a Blu-ray (registered trademark) medium. The removable recording medium 927 may be a CompactFlash (CF; registered trademark), a flash memory, an SD memory card (Secure Digital Memory Card), or the like. Alternatively, the removable recording medium 927 may be, for example, an electronic appliance or an IC card (Integrated Circuit Card) equipped with a non-contact IC chip.

The connection port 923 is a port for allowing devices to directly connect to the information processing apparatus 900. Examples of the connection port 923 include a USB (Universal Serial Bus) port, an IEEE 1394 port, a SCSI (Small Computer System Interface) port, and the like. Other examples of the connection port 923 include an RS-232C port, an optical audio terminal, an HDMI (High-Definition Multimedia Interface) port, and the like. With the externally connected device 929 connected to this connection port 923, the information processing apparatus 900 directly obtains various types of data from the externally connected device 929, and provides various types of data to the externally connected device 929.

The communication device 925 is a communication interface configured from, for example, a communication device for connecting to a communication network 931. The communication device 925 is, for example, a wired or wireless LAN (Local Area Network), a Bluetooth (registered trademark), a communication card for WUSB (Wireless USB), or the like. Alternatively, the communication device 925 may be a router for optical communication, a router for ADSL (Asymmetric Digital Subscriber Line), a modem for various communications, or the like. This communication device 925 can transmit and receive signals and the like in accordance with a predetermined protocol, such as TCP/IP, on the Internet and with other communication devices, for example. The communication network 931 connected to the communication device 925 is configured from a network or the like connected via wire or wirelessly, and may be, for example, the Internet, a home LAN, infrared communication, radio wave communication, satellite communication or the like.

Heretofore, an example of the hardware configuration of the information processing apparatus 900 has been shown. Each of the structural elements described above may be configured using a general-purpose material, or may be configured from hardware dedicated to the function of each structural element. Accordingly, the hardware configuration to be used can be changed as appropriate according to the technical level at the time of carrying out each of the embodiments described above.

4. Supplement (Example of Configuration and Advantage Effects of this Embodiment of Disclosure)

CONCLUSION

The embodiments of the disclosure have been described above. The embodiments of the disclosure may have various forms in addition to the above-described embodiments.

For example, in the configuration of the device in the information processing system, a process to be executed in the mobile device and a process to be executed in the server may be appropriately designed, for example, according to the capability or communication environment of each device. Functions of the server are not implemented in a single device, and may be distributed and implemented in a plurality of devices. In addition, a plurality of client devices may share data via the server, and share data by performing communication between the client devices.

In addition, the satisfaction degree information acquisition unit may not necessarily acquire a satisfaction degree from the user's input information. For example, the satisfaction degree acquisition unit may receive the user's biological information measured by a sensor and estimate the satisfaction degree from the biological information.

It should be understood by those skilled in the art that various modifications, combinations, sub-combinations and alterations may occur depending on design requirements and other factors insofar as they are within the scope of the appended claims or the equivalents thereof.

Additionally, the present technology may also be configured as below.

(1) An information processing apparatus comprising:
a processor to:
acquire information associated with behavior of a user and information associated with satisfaction degree of the user; and
analyze an association between the information associated with behavior and the information associated with satisfaction degree.

(2) The apparatus of (1), wherein the processor generates information that affects the behavior of the user in accordance with the association.

(3) The apparatus of (1) or (2), wherein the information associated with behavior is recognized by a behavior recognition algorithm.

(4) The apparatus of any one of (1) to (3), wherein the processor generates integrated behavior information by combining the information associated with behavior and the information associated with satisfaction degree.

(5) The apparatus of (4), wherein the integrated behavior information is generated by discretizing the information associated with satisfaction degree on a time axis.

(6) The apparatus of (5), wherein the integrated behavior information includes integrated behavior information of a missing part generated using the information associated with behavior.

(7) The apparatus of (6), wherein the apparatus is portable.

(8) The apparatus of any one of (1) to (7) further comprising:
a display control unit to generate display data based on information that affects the behavior of the user generated in accordance with the association.

(9) The apparatus of (8), wherein the display data indicates behavior information for the user in accordance with desirability of behavior for the user.

(10) The apparatus of (8) or (9), wherein the display data indicates behavior information for the user in association with a behavior score.

(11) The apparatus of (10), wherein the behavior score indicates a satisfaction degree.

(12) The apparatus of (10) or (11), wherein, when the score is selected from a display screen, a screen display associated with the score is displayed.

(13) The apparatus of any one of (8) to (12), wherein the display data indicates behavior determined to increase the satisfaction degree of the user.

(14) The apparatus of any one of (8) to (13), wherein the display data indicates at least one screen display selectable to set a desired ideal behavior plan.

(15) The apparatus of any one of (8) to (14), wherein the display data indicates a screen display through which a goal of behavior can be set.

(16) The apparatus of any one of (8) to (15), wherein the display data indicates information on a recommended behavior selectable as feedback information.

What is claimed is:

1. An information processing apparatus comprising:
a processor configured to:
acquire information associated with behavior of a user and information associated with a subjective satisfaction degree of the user in a period including the behavior input by selection by the user of an indication for inputting the subjective satisfaction degree;
analyze an association between the information associated with the behavior and the information associated with the subjective satisfaction degree; and
generate a behavior model of the user for display on a screen and indicating a body activity behavior pattern in relationship to subjective satisfaction over a predetermined time interval, based on integrated behavior information combining the information associated with the behavior and the information associated with the subjective satisfaction degree, in which the body activity behavior pattern includes a plurality of user body activity behaviors having different respective activity amounts set by the user as respective goals which is displayed on the screen with respective times set within the predetermined time interval for performing the goals, each of the plurality of user body activity behaviors being displayed with a total number of times the user achieved the goal of the user body activity behavior at the corresponding time and a numerical goal behavior score indicating how much the goal, when achieved, contributes to a higher satisfaction degree of the user.

2. The apparatus of claim 1, wherein the processor is configured to generate information that affects the behavior of the user in accordance with the association.

3. The apparatus of claim 1, wherein the information associated with the behavior is recognized by a behavior recognition algorithm.

4. The apparatus of claim 1, wherein the integrated behavior information is generated by discretizing the information associated with the subjective satisfaction degree on a time axis.

5. The apparatus of claim 4, wherein the integrated behavior information includes integrated behavior information of a missing part generated using the information associated with the behavior.

6. The apparatus of claim 1, wherein the apparatus is portable.

7. The apparatus of claim 1 further comprising:
a display control unit configured to generate display data based on information that affects the behavior of the user generated in accordance with the association.

8. The apparatus of claim 7, wherein the display data indicates behavior information for the user in accordance with desirability of behavior for the user.

9. The apparatus of claim 7, wherein the display data indicates behavior information for the user in association with a second behavior score.

10. The apparatus of claim 9, wherein the second behavior score indicates a satisfaction degree.

11. The apparatus of claim 9, wherein, when the second score is selected from a display screen, a screen display associated with the second score is displayed.

12. The apparatus of claim 7, wherein the display data indicates behavior determined to increase the subjective satisfaction degree of the user.

13. The apparatus of claim 7, wherein the display data indicates at least one screen display selectable to set a desired ideal behavior plan.

14. The apparatus of claim 7, wherein the display data indicates a screen display through which a goal of behavior can be set.

15. The apparatus of claim 7, wherein the display data indicates information on a recommended behavior selectable as feedback information.

16. An information processing apparatus comprising:
a processor configured to:
generate information that affects behavior of a user in accordance with an analyzed association between information associated with behavior of the user and information associated with a subjective satisfaction degree of the user in a period including the behavior input by selection by the user of an indication for inputting the subjective satisfaction degree, wherein the information associated with the behavior and the information associated with the subjective satisfaction degree are acquired; and
generate a behavior model of the user for display on a screen and indicating a body activity behavior pattern in relationship to subjective satisfaction over a predetermined time interval, based on integrated behavior information combining the information associated with the behavior and the information associated with the subjective satisfaction degree, in which the body activity behavior pattern includes a plurality of user body activity behaviors having different respective activity amounts set by the user as respective goals which is displayed on the screen with respective times set within the predetermined time interval for performing the goals, each of the plurality of user body activity behaviors being displayed with a total number of times the user achieved the goal of the user body activity behavior at the corresponding time and a numerical goal behavior score indicating an indication of how much the goal, when achieved, contributes to a higher satisfaction degree of the user.

17. A method of information processing comprising:
acquiring information associated with behavior of a user and information associated with a subjective satisfaction degree of the user in a period including the behavior input by selection by the user of an indication for inputting the subjective satisfaction degree;
analyzing, by a processor, an association between the information associated with the behavior and the information associated with the subjective satisfaction degree; and
generating, by the processor, a behavior model of the user for display on a screen and indicating a body activity behavior pattern in relationship to subjective satisfaction over a predetermined time interval, based on integrated behavior information combining the information associated with the behavior and the information associated with the subjective satisfaction degree, in which the body activity behavior pattern includes a plurality of user body activity behaviors having different respective activity amounts set by the user as respective goals which is displayed on the screen with respective times set within the predetermined time interval for performing the goals, each of the plurality of user body activity behaviors being displayed with a total number of times the user achieved the goal of the user body activity behavior at the corresponding time and a numerical goal behavior score indicating how much the goal, when achieved, contributes to a higher satisfaction degree of the user.

18. A non-transitory recording medium recorded with a program executable by a computer, the program comprising:
acquiring information associated with behavior of a user and information associated with a subjective satisfaction degree of the user in a period including the behavior input by selection by the user of an indication for inputting the subjective satisfaction degree;
analyzing an association between the information associated with the behavior and the information associated with the subjective satisfaction degree; and
generating a behavior model of the user for display on a screen and indicating a body activity behavior pattern in relationship to subjective satisfaction over a predetermined time interval, based on integrated behavior information by combining the information associated with the behavior and the information associated with the subjective satisfaction degree, in which the body activity behavior pattern includes a plurality of user body activity behaviors having different respective activity amounts set by the user as respective goals which is displayed on the screen with respective times set within the predetermined time interval for performing the goals, each of the plurality of user body activity behaviors being displayed with a total number of times the user achieved the goal of the user body activity behavior at the corresponding time and a numerical goal behavior score indicating how much the goal, when achieved, contributes to a higher satisfaction degree of the user.

19. The apparatus of claim 1, wherein the plurality of user body activity behaviors includes eating, exercise and wake up.

* * * * *